(12) United States Patent
Zhao et al.

(10) Patent No.: US 12,228,643 B2
(45) Date of Patent: Feb. 18, 2025

(54) MODULARIZED ACOUSTIC PROBE

(71) Applicant: DeepSight Technology, Inc., Los Altos, CA (US)

(72) Inventors: Danhua Zhao, San Jose, CA (US); Lan Yang, Clayton, MO (US); Jiangang Zhu, Saint Louis, MO (US)

(73) Assignee: DeepSight Technology, Inc., Santa Clara, CA (US)

( * ) Notice: Subject to any disclaimer, the term of this patent is extended or adjusted under 35 U.S.C. 154(b) by 95 days.

(21) Appl. No.: 17/244,605

(22) Filed: Apr. 29, 2021

(65) Prior Publication Data

US 2022/0350022 A1    Nov. 3, 2022

(51) Int. Cl.
*G01S 15/89*     (2006.01)
*G01S 7/52*      (2006.01)

(52) U.S. Cl.
CPC ........ *G01S 15/8927* (2013.01); *G01S 7/5208* (2013.01); *G01S 15/8913* (2013.01); *G01S 15/8968* (2013.01); *G01S 15/8918* (2013.01); *G01S 15/8922* (2013.01)

(58) Field of Classification Search
CPC ............. G01S 15/8927; G01S 15/8918; G01S 15/8922; G01S 7/5208
See application file for complete search history.

(56) References Cited

U.S. PATENT DOCUMENTS

| | | | | |
|---|---|---|---|---|
| 5,012,316 A | * | 4/1991 | Silvermint | A61N 1/36542 174/255 |
| 8,302,480 B2 | * | 11/2012 | Maris | G01N 29/0681 73/642 |
| 8,647,279 B2 | * | 2/2014 | Daft | G01S 15/8927 600/443 |

(Continued)

FOREIGN PATENT DOCUMENTS

WO    2021/055823 A2    3/2021

OTHER PUBLICATIONS

Basiri-Esfahani, S., Armin, A., Forstner, S. et al. Precision ultrasound sensing on a chip. Nat Commun 10, 132 (2019). https://doi.org/10.1038/s41467-018-08038-4 (Year: 2019).*

*Primary Examiner* — Isam A Alsomiri
*Assistant Examiner* — Joseph C Fritchman
(74) *Attorney, Agent, or Firm* — MEDLER FERRO WOODHOUSE & MILLS PLLC

(57) ABSTRACT

Techniques are described herein that are capable of providing a modularized acoustic probe that includes multiple acoustic transducers that have discrete substrates. A first acoustic transducer is configured to generate an acoustic signal and to transmit the acoustic signal toward an object. The second acoustic transducer is configured to detect a reflected acoustic signal, which results from the acoustic signal reflecting from the object, and to convert the reflected acoustic signal to an electrical signal. The first and second acoustic transducers have respective discrete substrates. In (Continued)

an example, the second acoustic transducer may not be configured to generate acoustic signals. In another example, the first and second acoustic transducers may be in respective first and second rows of a two-row transducer array. In accordance with this example, the first and second acoustic transducers may be designed to have an acoustic parameter having respective first and second parameter values.

36 Claims, 10 Drawing Sheets

(56) References Cited

U.S. PATENT DOCUMENTS

| | | | |
|---|---|---|---|
| 9,575,165 B2 | 2/2017 | Miller et al. | |
| 9,702,737 B2* | 7/2017 | Grubel | G02B 6/12007 |
| 9,874,631 B2 | 1/2018 | Miller et al. | |
| 10,168,428 B2 | 1/2019 | Savord | |
| 11,298,568 B2* | 4/2022 | Thapliyal | A61B 34/10 |
| 11,419,580 B2* | 8/2022 | Stigall | A61B 17/22012 |
| 2002/0080685 A1 | 6/2002 | Schmidt | |
| 2005/0057284 A1 | 3/2005 | Wodnicki | |
| 2005/0279807 A1 | 12/2005 | Johnson | |
| 2008/0095490 A1* | 4/2008 | Ashkenazi | G02B 6/138 |
| | | | 385/13 |
| 2010/0322029 A1* | 12/2010 | Vu | G01V 1/46 |
| | | | 367/25 |
| 2012/0071761 A1* | 3/2012 | Miller | A61B 8/4444 |
| | | | 600/459 |
| 2012/0238876 A1* | 9/2012 | Tanabe | G01S 15/8918 |
| | | | 600/444 |
| 2015/0045668 A1* | 2/2015 | Smith | A61B 8/4444 |
| | | | 600/447 |
| 2016/0206288 A1* | 7/2016 | Choi | A61B 8/5207 |
| 2017/0065836 A1 | 3/2017 | Reed et al. | |
| 2017/0205500 A1* | 7/2017 | Kiyose | G01S 7/52079 |
| 2017/0360415 A1* | 12/2017 | Rothberg | A61B 8/467 |

* cited by examiner

MODULARIZED ACOUSTIC PROBE

BACKGROUND

Acoustic imaging technology has been increasingly utilized in various fields including clinical applications. Acoustic imaging technology operates by transmitting acoustic signals toward an object and detecting resulting echo signals that reflect from the object. A representation of the echo signals typically is displayed as an image so that an observer can identify physical attributes of the object based on corresponding attributes of the image.

One example type of acoustic imaging technology is ultrasound imaging technology. Conventional ultrasound transducers are made of a single sensor material, such as a piezoelectric material, to simplify manufacturing processes. One commonly used piezoelectric material is lead zirconate titanate (PZT). Single crystal materials have recently gained momentum in ultrasound probe production because such materials often have wider bandwidth and higher sensitivity, as compared to some other materials. Another type of transducer material is silicon, which can be processed to make Capacitive Micromachined Ultrasound Transducer (CMUT) transducers and Piezoelectric Micromachined Ultrasonic Transducer (PMUT) transducers.

An optical sensor that is configured to support whispering gallery modes (WGMs) was recently introduced to the ultrasound imaging field. Such optical sensors typically include at least one optical waveguide and at least one optical resonator in a supporting structure in which a least one (e.g., each) optical resonator is configured to propagate the WGMs. These optical sensors have relatively wide bandwidth and relatively high sensitivity in comparison with other types of ultrasound sensors. Because of their relatively high sensitivity and relatively broad bandwidth, images produced by the optical sensors can have increased spatial resolution, penetration, signal-to-noise ratio (SNR), tissue harmonic imaging performance, and Doppler imaging performance, as compared to other types of ultrasound transducers. However, although such optical sensors can detect acoustic echo signals, they traditionally are incapable of generating acoustic waves.

SUMMARY

Various approaches are described herein for, among other things, providing a modularized acoustic probe that includes multiple acoustic transducers that have discrete substrates. A substrate of an acoustic transducer is a base material on which processing is performed to produce layer(s) of material(s) thereon. Examples of such processing include but are not limited to surface passivation, photolithography, ion implantation, etching, plasma ashing, thermal treatments, chemical vapor deposition (CVD), atomic layer deposition (ALD), physical vapor deposition (PVD), and molecular beam epitaxy (MBE). Each acoustic transducer may include a single discrete substrate or multiple discrete substrates. For instance, each of multiple sub-components of the acoustic transducer may have a respective discrete substrate.

In an example approach, a modularized acoustic probe includes a first acoustic transducer and a second acoustic transducer. The first acoustic transducer is configured to generate an acoustic signal (e.g., infrasound wave(s), human-audible wave(s), or ultrasound wave(s)) and to transmit the acoustic signal toward an object. The second acoustic transducer is configured to detect a reflected acoustic signal, which results from the acoustic signal reflecting from the object, and to convert the reflected acoustic signal to an electrical signal. The first acoustic transducer and the second acoustic transducer have respective discrete substrates.

In a first example implementation of this approach, the second acoustic transducer is not configured to generate acoustic signals.

In a second example implementation of this approach, the first acoustic transducer is in a first row of a two-row transducer array, and the second acoustic transducer is in a second row of the two-row transducer array. In accordance with this implementation, the first acoustic transducer is designed to have an acoustic parameter having a first parameter value, and the second acoustic transducer is designed to have the acoustic parameter having a second parameter value. The second parameter value is different from the first parameter value.

In an example approach of making a modularized acoustic probe, transducer sub-components having respective discrete substrates are fabricated. A first subset of the transducer sub-components is combined to form a first acoustic transducer that is configured to generate an acoustic signal and is further configured to transmit the acoustic signal toward an object. A second subset of the transducer sub-components is combined to form a second acoustic transducer that is configured to detect a reflected acoustic signal, which results from the acoustic signal reflecting from the object, and is further configured to convert the reflected acoustic signal to an electrical signal and is not configured to generate acoustic signals. The first transducer and the second transducer are combined to form the modularized acoustic probe.

In another example approach of making a modularized acoustic probe, transducer sub-components having respective discrete substrates are fabricated. A first subset of the transducer sub-components is combined to form a first acoustic transducer in a first row of a two-row transducer array. The first acoustic transducer is configured to generate an acoustic signal and further configured to transmit the acoustic signal toward an object. Combining the first subset of the transducer sub-components includes designing the first acoustic transducer to have an acoustic parameter having a first parameter value. A second subset of the transducer sub-components is combined to form a second acoustic transducer in a second row of the two-row transducer array. The second acoustic transducer is configured to detect a reflected acoustic signal, which results from the acoustic signal reflecting from the object, and further configured to convert the reflected acoustic signal to an electrical signal. Combining the second subset of the transducer sub-components includes designing the second acoustic transducer to have the acoustic parameter having a second parameter value that is different from the first parameter value. The first transducer and the second transducer are combined to form the modularized acoustic probe.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Moreover, it is noted that the invention is not limited to the specific embodiments described in the Detailed Description and/or other sections of this document. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate embodiments of the present invention and, together with the description, further serve to explain the principles involved and to enable a person skilled in the relevant art(s) to make and use the disclosed technologies.

Figure 1:
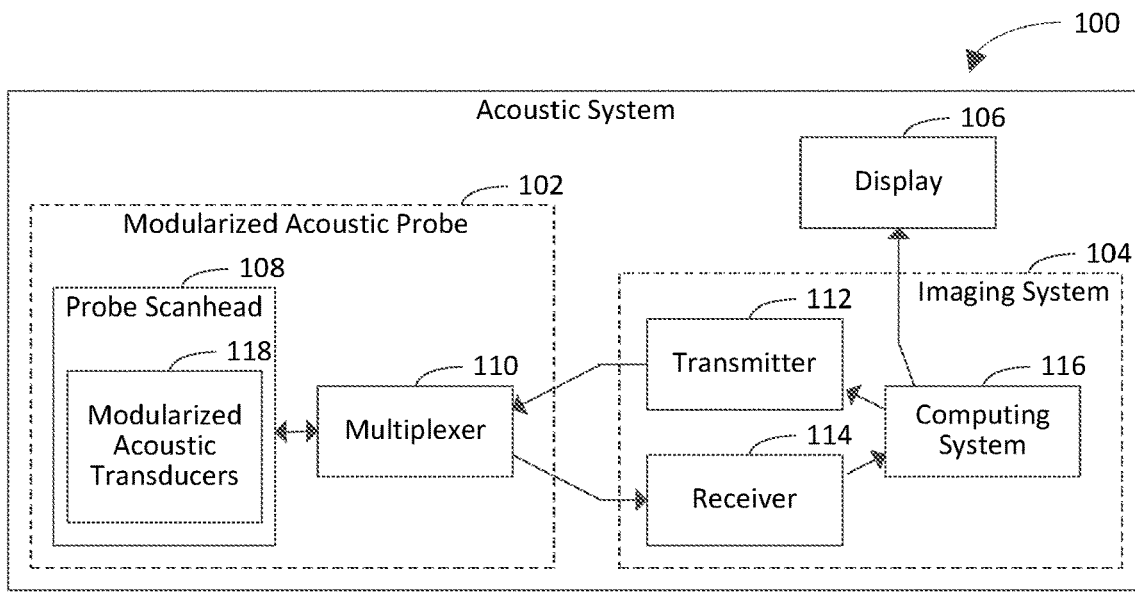
FIG. 1 is a block diagram of an example acoustic system that includes modularized acoustic transducers in accordance with an embodiment.

The features and advantages of the disclosed technologies will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

I. Introduction

The following detailed description refers to the accompanying drawings that illustrate exemplary embodiments of the present invention. However, the scope of the present invention is not limited to these embodiments, but is instead defined by the appended claims. Thus, embodiments beyond those shown in the accompanying drawings, such as modified versions of the illustrated embodiments, may nevertheless be encompassed by the present invention.

References in the specification to "one embodiment," "an embodiment," "an example embodiment," or the like, indicate that the embodiment described may include a particular feature, structure, or characteristic, but every embodiment may not necessarily include the particular feature, structure, or characteristic. Moreover, such phrases are not necessarily referring to the same embodiment. Furthermore, when a particular feature, structure, or characteristic is described in connection with an embodiment, it is submitted that it is within the knowledge of one skilled in the relevant art(s) to implement such feature, structure, or characteristic in connection with other embodiments whether or not explicitly described.

II. Example Embodiments

Example embodiments described herein are capable of providing a modularized acoustic probe that includes multiple acoustic transducers that have discrete substrates. A substrate of an acoustic transducer is a base material on which processing is performed to produce layer(s) of material(s) thereon. Examples of such processing include but are not limited to surface passivation, photolithography, ion implantation, etching, plasma ashing, thermal treatments, chemical vapor deposition (CVD), atomic layer deposition (ALD), physical vapor deposition (PVD), and molecular beam epitaxy (MBE). Each acoustic transducer may include a single discrete substrate or multiple discrete substrates. For instance, each of multiple sub-components of the acoustic transducer may have a respective discrete substrate.

Example modularized acoustic probes described herein have a variety of benefits as compared to conventional acoustic probes. For instance, the example modularized acoustic probes may be capable of increasing bandwidth and/or sensitivity, as compared to conventional acoustic probes, while being capable of generating acoustic signals and detecting acoustic signals. Accordingly, images produced by the example modularized acoustic probes may have increased spatial resolution, penetration, signal-to-noise ratio (SNR), tissue harmonic imaging performance, and Doppler imaging performance, as compared to conventional acoustic probes, without sacrificing the ability to generate acoustic waves.

The example modularized acoustic probes may include transducers (or transducer arrays) that are formed from respective types of substrates. For instance, a first subset of transducers may be formed from a first type of substrate, a second subset of the transducers may be formed from a second type of substrate that is different from the first type of substrate, and so on. Each subset of the transducers includes one or more of the transducers.

The example modularized acoustic probes may include transducers (or transducer arrays) that have respective types of transducer structure. For instance, one subset of transducers may have a first type of transducer structure, a second subset of the transducers may have a second type of transducer structure that is different from the first transducer structure, and so on.

An example modularized acoustic probe may include first transducer(s) that are configured to generate acoustic signals and second transducer(s) that are not configured to generate acoustic signals. For instance, the second transducer(s) may be capable of detecting acoustic signals more accurately, precisely, and/or efficiently than the first transducer(s). The first transducer(s) may be capable of generating acoustic signals more accurately, precisely, and/or efficiently than the second transducer(s).

An example modularized acoustic probe may include two arrays of transducers such that the transducers in the first array have a first type of transducer structure and the transducers in the second array have a second type of transducer structure. Having two arrays of transducers may cause the modularized acoustic probe to have a relatively lower complexity and/or cost than conventional 1.5D probes, which often include three or more arrays of transducers.

Example techniques described herein for making a modularized acoustic probe may provide a higher yield, as compared to conventional techniques for making an acoustic probe.

FIG. 1 is a block diagram of an example acoustic system 100 that includes modularized acoustic transducers 118 in accordance with an embodiment. The acoustic system 100 is operable to transmit acoustic signals (e.g., infrasound signals, human-audible signals, and/or ultrasound signals) toward an object, detect resulting echo signals that reflect from the object, and display a representation of the echo signals as an image. As shown in FIG. 1, the acoustic system 100 includes a modularized acoustic probe 102, an imaging system 104, and a display 106. The modularized acoustic probe 102 includes a probe scanhead 108 and a multiplexer 110. The probe scanhead 108 includes the modularized acoustic transducers 118. At least some of the modularized acoustic transducers 118 are operable during a transmit phase to convert electrical pulses that are received from the multiplexer 110 into acoustic waves and to transmit the acoustic waves toward object(s) in an environment of the acoustic system 100. At least some of the modularized acoustic transducers 118 are operable during a receive phase to detect the echo signals, which result from the acoustic waves reflecting from the object(s), and to convert the echo signals into electrical signals.

The multiplexer 110 includes analog switches that are configured to selectively connect channels of the imaging system 104 to desired modularized acoustic transducers in the probe scanhead 108. In the transmit phase, the multiplexer 110 forwards electrical pulses associated with the channels of the imaging system 104 to corresponding subsets of the modularized acoustic transducers 118. In the receive phase, the multiplexer 110 forwards electrical pulses from subsets of the modularized acoustic transducers 118 to the imaging system 104.

The imaging system 104 includes a transmitter 112, a receiver 114, and a computing system 116. The transmitter 112 generates electrical pulses that are provided to the multiplexer 110 to drive the modularized acoustic transducers 118. The receiver 114 receives electrical pulses from the multiplexer 110 and forwards those electrical pulses to the computing system 116 for processing. The computing system 116 provides output signals corresponding to the channels of the imaging system 104, which cause the transmitter 112 to generate the electrical pulses that are provided to the multiplexer 110. The computing system 116 also processes electrical pulses that are received from the receiver 114. For instance, the computing system 116 generates image pixels based on the electrical pulses that are received from the receiver 114.

The display 106 converts the image pixels that are received from the computing system 116 to display pixels. The display 106 displays the display pixels to form an image of the object(s).

Figure 2:
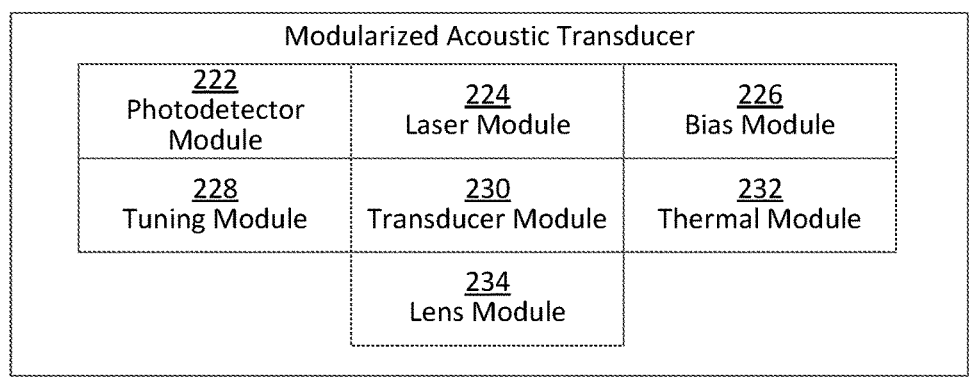
FIG. 2 is a block diagram of an example modularized acoustic transducer in accordance with an embodiment.

FIG. 2 is a block diagram of an example modularized acoustic transducer 200 in accordance with an embodiment. For instance, the modularized acoustic transducer 200 may be an example implementation of one of the modularized acoustic transducers 118 shown in FIG. 1. The modularized acoustic transducer 200 includes a photodetector module 222, a laser module 224, a bias module 226, a tuning module 228, a transducer module 230, a thermal module 232, and a lens module 234. The photodetector module 222 includes at least one photodetector, which converts optical signals into electrical signals. For instance, the optical signal may be a laser beam that is modulated by a reflected acoustic signal, which has been reflected from an object (e.g., tissue or bone). The laser module 224 includes at least one laser, which transmits a laser beam to optical sensor elements. For example, the optical sensor elements may be included in the transducer module 230. In accordance with this example, the transducer module 203 may be an acousto-optic sensor module that includes at least one acousto-optic sensor, which converts an acoustic signal to an optical signal. For instance, the acoustic signal may be the aforementioned reflected acoustic signal, which has been reflected from the object. The bias module 226 includes at least one bias circuit, which provides bias voltages to transducer elements in the transducer module 230 that require bias voltages. The tuning module 228 includes at least one tuning circuit, which performs impedance matching between transducer elements in the transducer module 230 and channels of an imaging system (e.g., imaging system 104).

The transducer module 230 includes a transducer having at least one transducer element. For example, the transducer module 230 may include a single transducer element. In another example, the transducer module 230 may include multiple transducer elements (e.g., an array of transducer elements). Each transducer element converts electric signals to acoustic signals and/or converts acoustic signals to electric signals. Each transducer element may include multiple sub-elements, though the scope of the example embodiments is not limited in this respect. The transducer module 230 may be configured in any of a variety of ways. For example, the transducer module 230 may be configured to be an acousto-optic sensor module (as mentioned above), a whispering gallery mode (WGM) resonator module, etc. A WGM resonator module includes at least one WGM resonator, which supports WGMs and modulates the laser beam that is transmitted by the laser module 224.

The thermal module 232 includes at least one thermal circuit, which regulates temperature inside a probe scanhead (e.g., probe scanhead 108) that includes the modularized acoustic transducer 200. The lens module 234 includes at least one lens, which provides mechanical focusing of acoustic signals that are transmitted and/or received by the transducer module 230.

The modularized acoustic transducer 200 is shown to include seven modules 222, 224, 226, 228, 230, 232, and 234 for non-limiting, illustrative purposes. It will be recognized that the modularized acoustic transducer 200 may include any suitable number of modules (e.g., 1, 2, 3, 4, 5, . . . ). Moreover, each of the modules 222, 224, 226, 228, 230, 232, and 234 may be divided into multiple smaller modules. It will be further recognized that the modularized acoustic transducer 200 need not necessarily include any one or more of the photodetector module 222, the laser module 224, the bias module 226, the tuning module 228, the transducer module 230, the thermal module 232, and/or the lens module 234. For instance, in an example embodiment, the modularized acoustic transducer 200 consists of five modules: the photodetector module 222, the laser module 224, the transducer module 230, the thermal module 232, and the lens module 234. Moreover, the modularized acoustic transducer 200 may include module(s) in addition to or in lieu of the photodetector module 222, the laser module 224, the bias module 226, the tuning module 228, the transducer module 230, the thermal module 232, and/or the lens module 234. The modules 222, 224, 226, 228, 230, 232, and 234 may be built at the same time and in the same place, or at different times and in different places before being assembled to form the modularized acoustic transducer 200.

Figure 3:
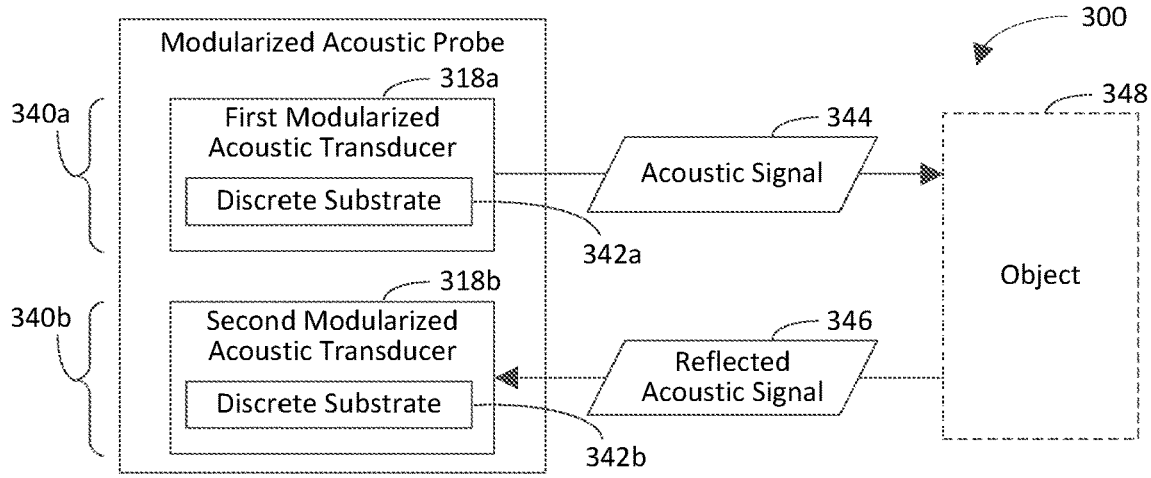
FIG. 3 is a block diagram of an example modularized acoustic probe that includes first and second modularized acoustic transducers in accordance with an embodiment.

FIG. 3 is a block diagram of an example modularized acoustic probe 300 in accordance with an embodiment. The modularized acoustic probe 300 includes a first modularized acoustic transducer 318a and a second modularized acoustic transducer 318b. The first modularized acoustic transducer 318a is configured to generate an acoustic signal 344 and to transmit the acoustic signal 344 toward an object 348. The first modularized acoustic transducer 318a has a discrete substrate 342a. The second modularized acoustic transducer 318b is configured to detect a reflected acoustic signal 346, which results from the acoustic signal 344 reflecting from the object 348, and to convert the reflected acoustic signal 346 to an electrical signal. The second modularized acoustic transducer 318b has a discrete substrate 342b. Each of the first and second modularized acoustic transducers 318a-318b is shown to include a single discrete substrate for non-limiting illustrative purposes. It will be recognized that each of the first and second modularized acoustic transducers 318a-318b may include any suitable number (e.g., 1, 2, 3, 4, 5, . . . ) of discrete substrates, so long as each of the first and second modularized acoustic transducers 318a-318b includes at least one discrete substrate. For instance, each of the first and second modularized acoustic transducers 318a-318b may include a discrete substrate for each module (e.g., photodetector module 222, laser module 224, bias module 226, tuning module 228, transducer module 230, thermal module 232, and/or lens module 234) that is included in the respective modularized acoustic transducer.

In an example embodiment, the second modularized acoustic transducer 318b is not configured to generate acoustic signals. For example, the second modularized acoustic transducer 318b may be configured to not generate acoustic signals. In accordance with this example, the second modularized acoustic transducer 318b may include transducer element(s) that are configured to generate acoustic signals, and the transducer element(s) may be disabled. In another example, the second modularized acoustic transducer 318b may be incapable (e.g., inherently incapable) of generating acoustic signals. In accordance with this example, the material from which the second modularized acoustic transducer 318b is formed may not be capable of generating acoustic signals.

In another example embodiment, the first modularized acoustic transducer 318a is in a first row 340a of a two-row transducer array, and the second modularized acoustic transducer 318b in a second row 340b of the two-row transducer array. In accordance with this embodiment, the first modularized acoustic transducer 318a is designed to have an acoustic parameter having a first parameter value, and the second modularized acoustic transducer 318b is designed to have the acoustic parameter having a second parameter value that is different from the first parameter value. Examples of an acoustic parameter include but are not limited to center frequency, resonant frequency, dynamic range, and quality factor (Q). For example, the first modularized acoustic transducer 318a may be designed to have a center frequency or a resonant frequency of X, and the second modularized acoustic transducer 318b may be designed to have a center frequency or a resonant frequency of X*Y, where X is any suitable positive number (e.g., 3 MHz, 3.5 MHz, 6 MHz, or 7.5 MHz) and Y is any suitable positive number (e.g., 2, 12/7, 15/7, 2.5, or 3). In accordance with this embodiment, each of the first and second rows 340a-340b may be linear or curved. In further accordance with this embodiment, the first and second modularized acoustic transducers 318a-318b may be configured to cause a difference between the first parameter value and the second parameter value to be at least a threshold difference.

In yet another example embodiment, the second modularized acoustic transducer 318b includes an acousto-optic sensor, a laser (e.g., laser module 224), and a photodetector (e.g., photodetector module 222). The acousto-optic sensor is configured to convert the reflected acoustic signal 346 to an optical signal. The laser is configured to generate a laser beam to actuate the acousto-optic sensor. The photodetector is configured to detect the laser modulated by the reflected acoustic signal 346. For instance, the frequency or intensity of the laser may be modulated by the reflected acoustic signal 236. In accordance with this embodiment, the second modularized acoustic transducer 318b may include whispering gallery mode (WGM) resonators that are configured to modulate the laser beam.

In still another example embodiment, the first modularized acoustic transducer 318a is further configured to convert the reflected acoustic signal to a second electrical signal.

In another example embodiment, the first modularized acoustic transducer 318a has a first type of transducer structure, and the second acoustic transducer 318b has a second type of transducer structure that is different from the first type of transducer structure. Example types of transducer structure include but are not limited to lead zirconate titanate (PZT), single crystal (e.g., Si), Capacitive Micromachined Ultrasound Transducer (CMUT), and Piezoelectric Micromachined Ultrasonic Transducer (PMUT).

In yet another example embodiment, the modularized acoustic probe 300 includes multiple implementations of the first modularized acoustic transducer 318a and multiple implementations of the second modularized acoustic transducer 318b. For example, the first modularized acoustic transducers may be included in a first array, and the second modularized acoustic transducers may be included in a second array. In accordance with this example, the first array may be included in the first row 340a, and the second array may be included in the second row 340b. In further accordance with this embodiment, each first modularized acoustic transducer in the first array is configured to generate a respective acoustic signal and to transmit the respective acoustic signal toward the object 348. In further accordance with this embodiment, each second modularized acoustic transducer in the second array is configured to detect reflected acoustic signals, which result from the respective acoustic signals reflecting from the object 348, and to convert the reflected acoustic signals to a respective electrical signal.

In an aspect of this embodiment, the modularized acoustic probe 300 further includes a third array of third modularized acoustic transducers such that each third modularized acoustic transducer in the third array is configured to generate a respective acoustic signal and/or convert the reflected acoustic signals to an electrical signal. In accordance with this aspect, each first modularized acoustic transducer, each second modularized acoustic transducer, and each third modularized acoustic transducer has a respective discrete substrate. In a first example implementation, each of the first array, the second array, and the third array is a curvilinear array, and each curvilinear array has a curved shape. In a second example implementation, each of the first array, the second array, and the third array is a linear array, and each linear array has a linear shape.

In another example embodiment, modularized acoustic probe 300 includes a first number of first acoustic transducers and a second number of second acoustic transducers. The first number and the second number are not same. In accordance with this embodiment, each first acoustic transducer is configured to generate a respective acoustic signal and to transmit the respective acoustic signal toward the object 348. In further accordance with this embodiment, each second acoustic transducer is configured to detect reflected acoustic signals, which result from the respective acoustic signals reflecting from the object 348, and to convert the reflected acoustic signals to a respective electrical signal. Each first acoustic transducer and each second acoustic transducer has a respective discrete substrate.

In yet another example embodiment, the modularized acoustic probe 300 is in a shape of a disk. In accordance with this embodiment, the first modularized acoustic transducer 318a forms a first portion of the disk. In further accordance with this embodiment, the second modularized acoustic transducer 318b forms a second portion of the disk.

In still another example embodiment, the first modularized acoustic transducer 318a forms a ring around the second modularized acoustic transducer 318b, or the second modularized acoustic transducer 318b forms a ring around the first modularized acoustic transducer 318a.

Figure 4:
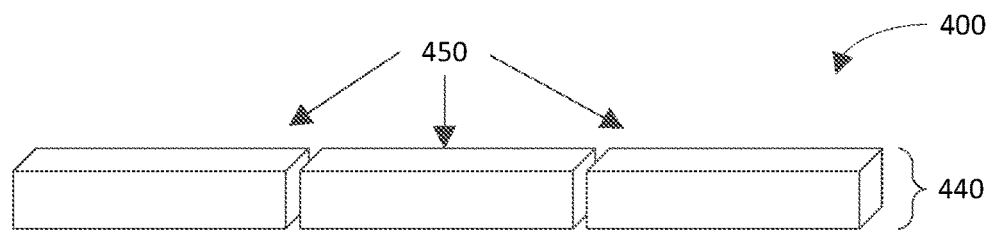
FIG. 4 illustrates an example single-row transducer array.

FIG. 4 illustrates an example single-row transducer array 400. The single-row transducer array 400 includes multiple transducer modules 450 arranged in a single row 440. Each of the transducer modules 450 may include a single transducer element or multiple transducer elements. In an example implementation, the transducer modules 450 have a common acoustic design. In accordance with this implementation, the transducer modules 450 may be interchangeable with each other. In another example implementation, any one or more of the transducer modules 450 may have an acoustic design that is different from an acoustic design of any one or more of the other transducer modules. For example, individual transducer modules may have different frequencies and pitches. Each of the transducer modules 450 may be capable of generating and detecting acoustic signals. For instance, each of the transducer modules 450 may be capable of generating and detecting a designated type of acoustic signals. Example types of acoustic signals include but are not limited to infrasound signals, human-audible signals, and ultrasound signals. The single-row transducer array 400 is shown to include three transducer modules for non-limiting, illustrative purposes. It will be recognized that the single-row transducer 400 may include any suitable number (e.g., 1, 2, 3, 4, 5, . . . ) of transducer modules. The transducer modules 450 may have respective discrete substrates.

Figure 5:
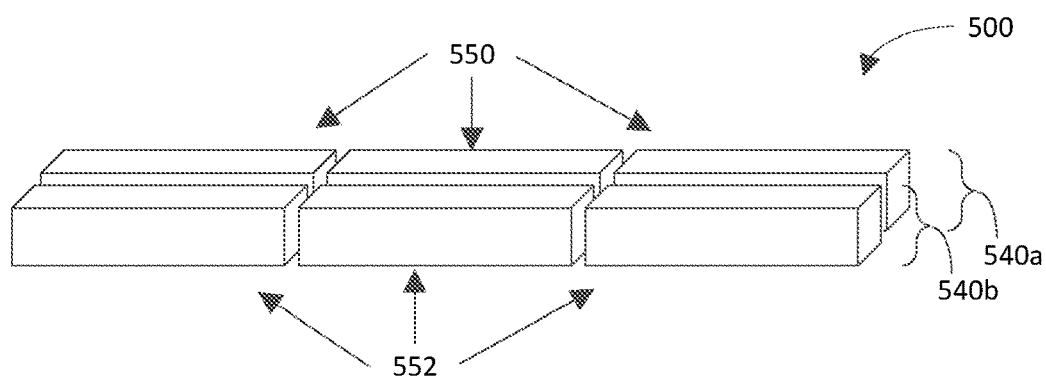
FIGS. 5-6 illustrate example two-row transducer arrays in accordance with embodiments.

FIG. 5 illustrates an example two-row transducer array 500 in accordance with an embodiment. The two-row transducer array 500 includes first transducer modules 550 arranged in a first row 540a and second transducer modules 552 arranged in a second row 540b. In an example implementation, the first transducer modules 550 have a first common (e.g., same) acoustic design, and the second transducer modules 552 have a second common acoustic design that is different from the first common acoustic design. For example, the first transducer modules 550 may be designed to generate acoustic signals, and the second transducer modules 552 may not be designed to generate acoustic signals. In an aspect of this example, the first transducer modules 550 may be designed to generate acoustic signals and not to convert acoustic signals to an electric signal, and the second transducer modules 552 may be designed to convert acoustic signals to an electric signal and not to generate acoustic signals. In another aspect of this example, the first transducer modules 550 may be designed to generate acoustic signals and to convert acoustic signals to an electrical signal, and the second transducer modules 552 may be designed to convert acoustic signals to an electrical signal and not to generate acoustic signals. In another example, the first transducer modules 550 may be designed to generate acoustic signals and not to convert acoustic signals to an electric signal, and the second transducer modules 552 may be designed to generate acoustic signals and to convert acoustic signals to an electric signal. It will be recognized that the first transducer modules 550 may be designed to generate acoustic signals and to convert acoustic signals to an electric signal, and the second transducer modules 552 may be designed to generate acoustic signals and to convert acoustic signals to an electric signal.

In another example, the first transducer modules 550 may be designed to have an acoustic parameter having a first parameter value, and the second transducer modules 552 may be designed to have the acoustic parameter having a second parameter value that is different from the first parameter value. For instance, the first transducer modules 550 may have a first center frequency (e.g., 6 MHz), and the second transducer modules 552 may have a second center frequency (e.g., 12 MHz) that is different from the first center frequency. The second transducer modules 552 may be made of a different material than the first transducer modules 550. In an example implementation, the first transducer modules 550 are made of CMUT, PMUT, or PZT, and the second transducer modules 552 are made of optical sensors such as WGM resonators. In an example embodiment, the first transducer modules 550 are dedicated for generation of acoustic signals, and the second transducer modules 552 are dedicated for detection of acoustic signals. Each of the first row 540a and the second row 540b is shown to include three transducer modules for non-limiting, illustrative purposes. It will be recognized that each of the rows 540a-540b may include any suitable number (e.g., 1, 2, 3, 4, 5, . . . ) of transducer modules.

Figure 6:
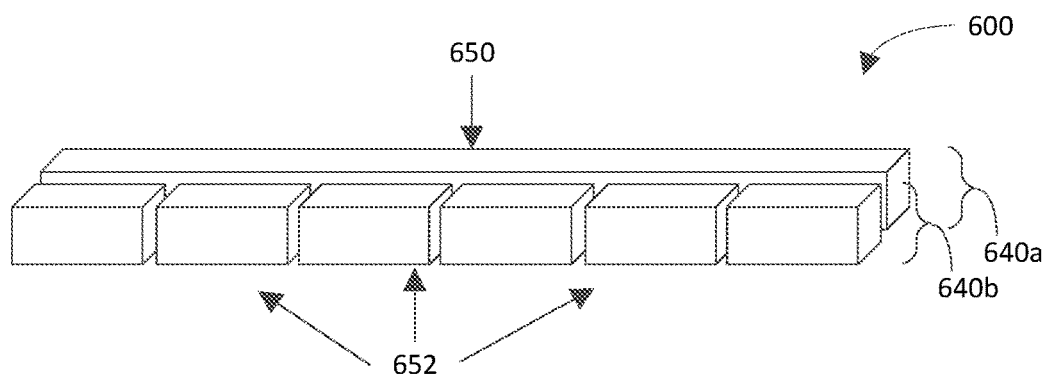

FIG. 6 illustrates another example two-row transducer array 600 in accordance with an embodiment. FIG. 6 differs from FIG. 5 only in the number of transducer modules on each row. Although the number is the same for each row in FIG. 5, the number varies from row to row in FIG. 6. As shown in FIG. 6, the two-row transducer array 600 includes a single first transducer module 650 arranged in a first row 640*a* and multiple second transducer modules 652 arranged in a second row 640*b*. In an example implementation, the second transducer modules 652 have a second common acoustic design that is different from the acoustic design of the first transducer modules 650. The first row 640*a* is shown to include one transducer module 650, and the second row 640*b* is shown to include six transducer modules, for non-limiting, illustrative purposes. It will be recognized that each of the rows 640*a*-640*b* may include any suitable number (e.g., 1, 2, 3, 4, 5, . . . ) of transducer modules. For instance, the first row 640*a* may include two transducer modules, and the second row 640*b* may include five transducer modules.

Figure 7:
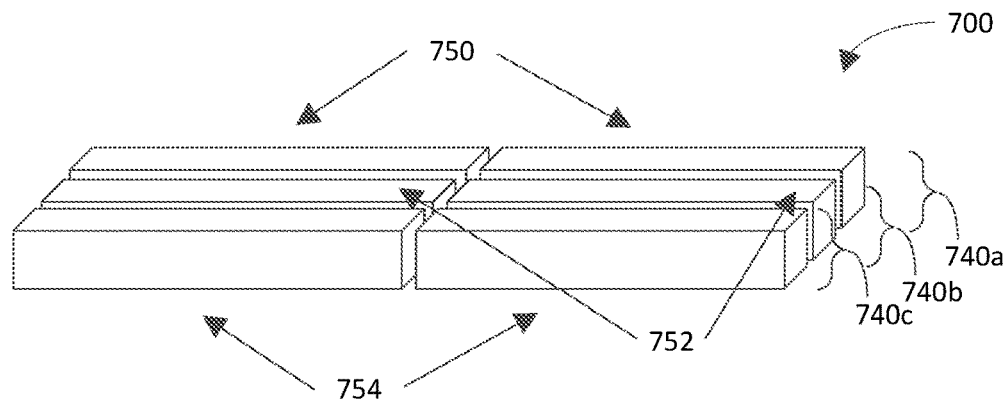
FIG. 7 illustrates an example three-row transducer array in accordance with an embodiment.

FIG. 7 illustrates an example three-row transducer array 700 in accordance with an embodiment. The three-row transducer array 700 includes first transducer modules 750 arranged in a first row 740*a*; second transducer modules 752 arranged in a second row 740*b*; and third transducer modules 754 arranged in a third row 740*c*. In the embodiment of FIG. 7, the second row 740*b* is located between the first row 740*a* and the third row 740*c*. In an example implementation, the first transducer modules 750 have a first common acoustic design; the second transducer modules 752 have a second common acoustic design; and the third transducer modules 754 have a third common acoustic design. In an example, the first transducer modules 750 may be designed to have an acoustic parameter having a first parameter value; the second transducer modules 752 may be designed to have the acoustic parameter having a second parameter value that is different from the first parameter value; and the third transducer modules 754 may be designed to have the acoustic parameter having a third parameter value that is different from the first and second parameter values. For instance, the first transducer modules 750 may have a first center frequency (e.g., 15 MHz); the second transducer modules 752 may have a second center frequency (e.g., 7.5 MHz) that is different from the first center frequency; and the third transducer modules 754 may have a third center frequency (e.g., 3.5 MHz) that is different from the first center frequency and the second center frequency. The third transducer modules 754 may be made of a different material than the second transducer modules 752, which may be made of a different material than the first transducer modules 750. In an example implementation, the first transducer modules 750 are made of optical sensors such as WGM resonators; the second transducer modules 752 are made of PZT; and the third transducer modules 754 are made of CMUT or PMUT.

In an example embodiment, the transducer modules in one of the rows 740*a*-740*c* is dedicated for generation of acoustic signals, and the transducer modules in the other two rows are dedicated for detection of acoustic signals. For example, the second transducer modules 752, which are in the second row 740*b*, may be used to generate acoustic waves and not to detect acoustic waves. In accordance with this example, the first transducer modules 750 and the third transducer modules 754, which are in the respective first and third rows 740*a* and 740*c*, may be used to detect acoustic waves and not to generate acoustic waves. Each of the first row 740*a*, the second row 740*b*, and the third row 740*c* is shown to include two transducer modules for non-limiting, illustrative purposes. It will be recognized that each of the rows 740*a*-740*c* may include any suitable number (e.g., 1, 2, 3, 4, 5, . . . ) of transducer modules. Moreover, the number of transducer modules may vary from row to row. For example, the first row 740*a* may include one transducer module; the second row 740*b* may include four transducer modules; and the third row 740*c* may include two transducer modules.

Figure 8:
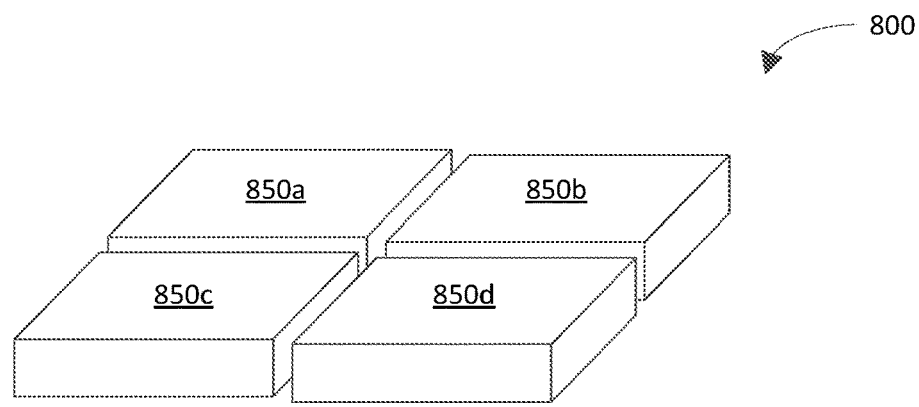
FIG. 8 illustrates an example two-dimensional (2D) transducer array in accordance with an embodiment.

FIG. 8 illustrates an example two-dimensional (2D) transducer array 800 in accordance with an embodiment. The 2D transducer array 800 includes 2D transducer modules 850*a*-850*d*. The 2D transducer modules 850*a*-850*d* have a common acoustic design. Accordingly, the 2D transducer modules 850*a*-850*d* may be interchangeable with each other. Each of the 2D transducer modules 850*a*-850*d* may be capable of generating and detecting acoustic signals. The number of transducer elements in each of the 2D transducer modules may vary from 16×16=256 to any positive integer n>256. The 2D transducer array 800 includes four 2D transducer modules for non-limiting, illustrative purposes. It will be recognized that the 2D transducer array 800 may include any suitable number of 2D transducer modules in any suitable number of rows and any suitable number of columns. For instance, the 2D transducer array 800 may include three rows and four columns for a total of 3*4=12 2D transducer modules.

Figure 9:
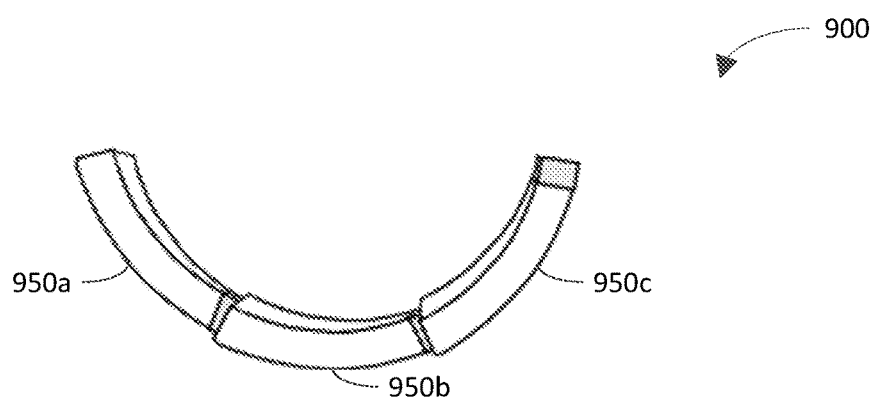
FIG. 9 illustrates an example one-dimensional (1D) curvilinear transducer array in accordance with an embodiment.

FIG. 9 illustrates an example one-dimensional (1D) curvilinear transducer array 900 in accordance with an embodiment. The 1D curvilinear transducer array 900 includes 1D transducer modules 950*a*-950*c*. The 1D transducer modules 950*a*-950*c* have a common acoustic design. Accordingly, the 1D transducer modules 950*a*-950*c* may be interchangeable with each other. Each of the 1D transducer modules 950*a*-950*c* may be capable of generating and detecting acoustic signals. The 1D curvilinear transducer array 900 includes three 1D transducer modules for non-limiting, illustrative purposes. It will be recognized that the 1D curvilinear transducer array 900 may include any suitable number (e.g., 1, 2, 3, 4, 5, . . . ) of 1D transducer modules. The transducer modules 950*a*-950*c* may have respective discrete substrates. It will be recognized that the multiple-row configurations shown in FIGS. 5-7 may be extended to curvilinear transducer arrays, as well.

Figure 10:
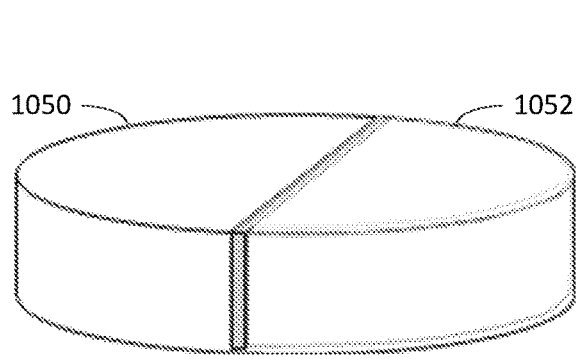
FIG. 10 illustrates an example circular transducer array in accordance with an embodiment.

FIG. 10 illustrates an example circular (a.k.a. disk) transducer array 1000 in accordance with an embodiment. The circular transducer array 1000 includes a first transducer module 1050 and a second transducer module 1052. In an example implementation, the first transducer module 1050 has a first acoustic design, and the second transducer module 1052 has a second acoustic design that is different from the first acoustic design. For example, the first transducer module 1050 may be designed to generate acoustic signals, and the second transducer module 1052 may not be designed to generate acoustic signals. In another example, the first transducer module 1050 may be designed to have an acoustic parameter having a first parameter value, and the second transducer module 1052 may be designed to have the acoustic parameter having a second parameter value that is different from the first parameter value. For instance, the first transducer module 1050 may have a first center frequency (e.g., 6 MHz), and the second transducer module 1052 may have a second center frequency (e.g., 12 MHz) that is different from the first center frequency. The first transducer module 1050 may be made of a first material, and the second transducer module 1052 may be made of a second material that is different from the first material. In an example implementation, the first transducer module 1050 is made of CMUT, PMUT, or PZT, and the second transducer module 1052 is made of an optical sensor such as a WGM resonator. In an example embodiment, the first transducer module 1050 is configured to generate acoustic signals and not to detect acoustic signals, and the second transducer module 1052 is configured to detect acoustic signals and not to generate acoustic signals. In an example embodiment, the first transducer module 1050 includes a single transducer element, and the second transducer module 1052 includes a single transducer element.

Figure 11:
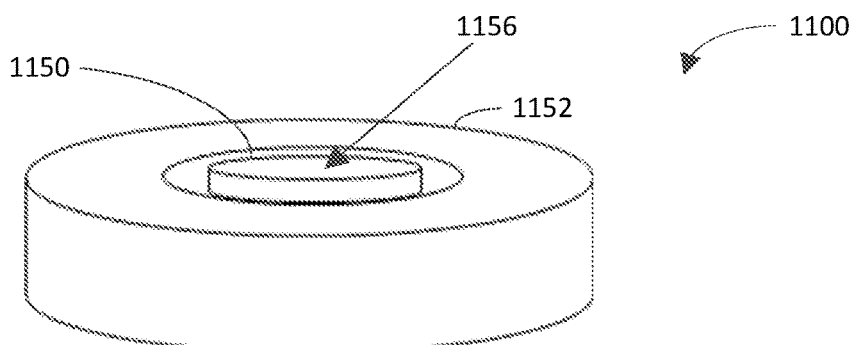
FIG. 11 illustrates an example annular transducer array in accordance with an embodiment.

FIG. 11 illustrates an example annular transducer array 1100 in accordance with an embodiment. The annular transducer array 1100 includes a first transducer module 1150 and a second transducer module 1152. In an example implementation, the first transducer module 1150 has a first acoustic design, and the second transducer module 1152 has a second acoustic design that is different from the first acoustic design. For example, the first transducer module 1150 may be designed to generate acoustic signals, and the second transducer module 1152 may not be designed to generate acoustic signals, or vice versa. In another example, the first transducer module 1150 may be designed to have an acoustic parameter having a first parameter value, and the second transducer module 1152 may be designed to have the acoustic parameter having a second parameter value that is different from the first parameter value. For instance, the first transducer module 1150 may have a first center frequency (e.g., 6 MHz), and the second transducer module 1152 may have a second center frequency (e.g., 12 MHz) that is different from the first center frequency, or vice versa.

The first transducer module 1150 may be made of a first material, and the second transducer module 1152 may be made of a second material that is different from the first material. In an example implementation, the first transducer module 1150 is made of CMUT, PMUT, or PZT, and the second transducer module 1152 is made of an optical sensor such as a WGM resonator, or vice versa. In an example embodiment, the first transducer module 1150 is configured to generate acoustic signals and not to detect acoustic signals, and the second transducer module 1152 is configured to detect acoustic signals and not to generate acoustic signals. In another example embodiment, the first transducer module 1150 is configured to detect acoustic signals and not to generate acoustic signals, and the second transducer module 1152 is configured to generate acoustic signals and not to detect acoustic signals. In yet another example embodiment, the first transducer module 1150 is configured to generate acoustic signals and to detect acoustic signals, and the second transducer module 1152 is configured to detect acoustic signals and not to generate acoustic signals. In still another example embodiment, the first transducer module 1150 is configured to detect acoustic signals and not to generate acoustic signals, and the second transducer module 1152 is configured to generate acoustic signals and to detect acoustic signals. In another example embodiment, the first transducer module 1150 is configured to generate acoustic signals and not to detect acoustic signals, and the second transducer module 1152 is configured to generate acoustic signals and to detect acoustic signals. In yet another example embodiment, the first transducer module 1150 is configured to generate acoustic signals and to detect acoustic signals, and the second transducer module 1152 is configured to generate acoustic signals and not to detect acoustic signals.

The annular transducer array 1100 is shown to include two transducer modules for non-limiting, illustrative purposes. It will be recognized that the annular transducer array 1100 may include any suitable number (e.g., 1, 2, 3, 4, 5, . . . ) of transducer modules. For instance, the second transducer module 1152 is shown to surround the first transducer module 1150 in a plane that is parallel with a circular surface 1156 of the first transducer module 1150 in FIG. 11. A third transducer module may surround the second transducer module 1152 in the plane, a fourth transducer module may surround the third transducer module in the plane, and so on. Accordingly, the transducer modules may form concentric circles in the plane. In an example embodiment, the first transducer module 1150 includes a single transducer element, and the second transducer module 1152 includes a single transducer element.

Figure 12:
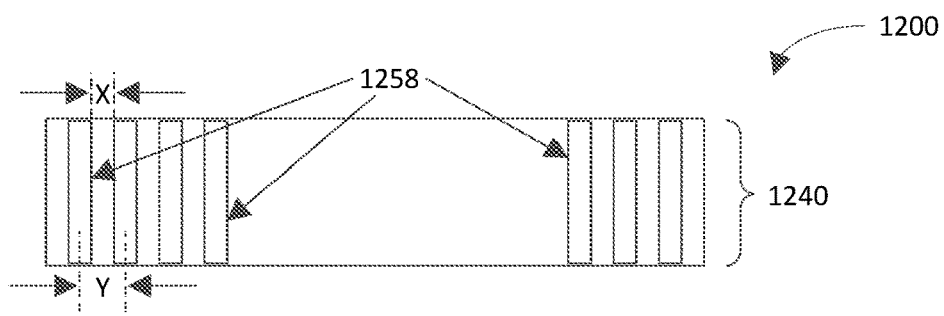
FIG. 12 illustrates an example modularized acoustic probe that includes a single row of transducers in accordance with an embodiment.

FIG. 12 illustrates an example transducer module 1200 that includes a single row 1240 of transducer elements 1258 in accordance with an embodiment. In an example implementation, the transducer elements 1258 have a common acoustic design. For instance, the transducer elements 1258 may be designed to be identical. In another example implementation, a distance (a.k.a. gap), X, between adjacent transducer elements is a constant. In yet another example implementation, a distance (a.k.a. pitch), Y, between centers of adjacent transducer elements is a constant. An entirety of each transducer element is active. Accordingly, each transducer element is capable of generating acoustic signals and/or detecting acoustic signals. Each transducer element may have any suitable acoustic structure, including but not limited to PZT, single crystal, CMUT, PMUT, and/or optical sensor.

Figure 13:
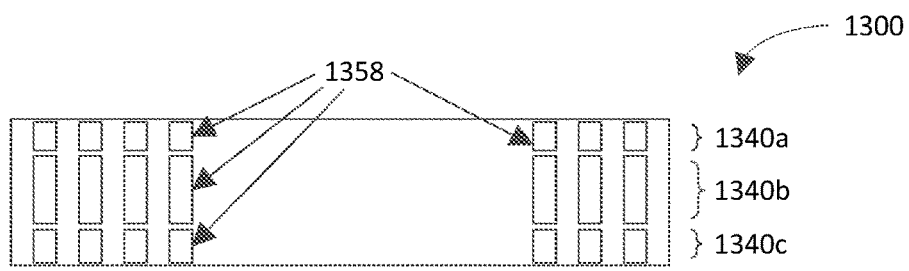
FIG. 13 illustrates an example modularized acoustic probe that includes three rows of transducers in accordance with an embodiment.

FIG. 13 illustrates an example transducer module 1300 that includes three rows 1340a-1340c of transducer sub-elements 1358 in accordance with an embodiment. Each row includes the same number of the transducer sub-elements 1358 for non-limiting, illustrative purposes. It will be recognized that each row may include a different number of the transducer sub-elements 1358 than other row(s). The transducer module 1300 includes a single row of transducer elements, and each of the transducer elements includes three sub-elements for non-limiting, illustrative purposes. It will be recognized that each of the transducer elements may include any suitable number of sub-elements (e.g., 1, 2, 3, 4, 5, . . . ). In an example implementation, the pitch (i.e., the distance between centers of adjacent transducer sub-elements) in each row is constant. The pitch among the rows is the same. A size of the transducer sub-elements 1358 may vary from row to row, as shown in FIG. 13, though the example embodiments are not limited in this respect. An entirety of each transducer sub-element is active. Accordingly, each of the transducer sub-elements 1358 is capable of generating acoustic signals and/or detecting acoustic signals. Each transducer sub-element may have any suitable acoustic structure, including but not limited to PZT, single crystal, CMUT, PMUT, and/or optical sensor.

Figure 14:
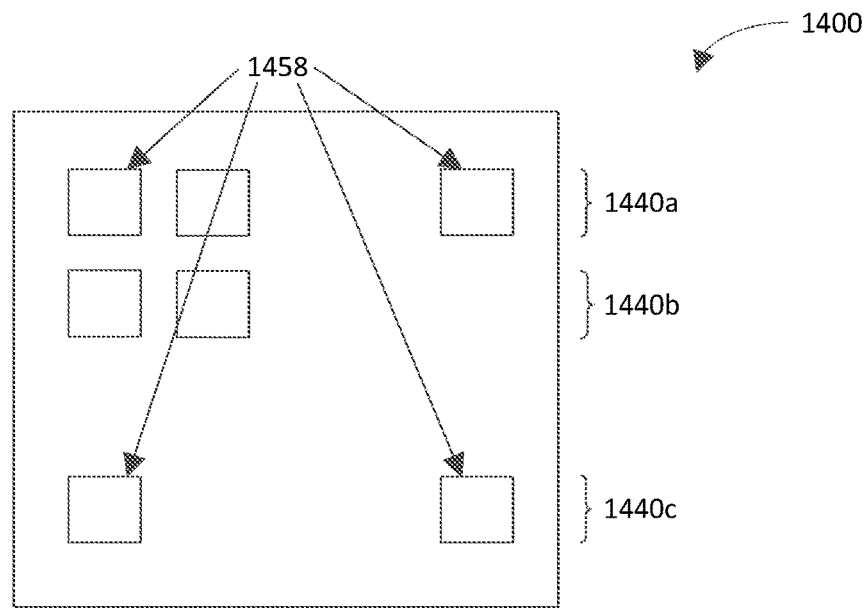
FIG. 14 illustrates an example modularized acoustic probe that includes multiple rows of 2D transducers in accordance with an embodiment.

FIG. 14 illustrates an example transducer module 1400 that includes multiple rows 1440a-1440c of 2D transducer elements 1458 in accordance with an embodiment. In an example implementation, the transducer elements 1458 have a common acoustic design. For instance, the transducer elements 1458 may be designed to be identical. In another example implementation, the pitch (i.e., the distance between centers of adjacent transducer elements) is constant in both vertical and horizontal dimensions. In yet another example implementation, the pitch in the vertical dimension is different form the pitch in the horizontal dimension. For instance, the pitch in the horizontal dimension may be 0.2 mm, and the pitch in the vertical dimension may be 0.25 mm, or vice versa.

Figure 15:
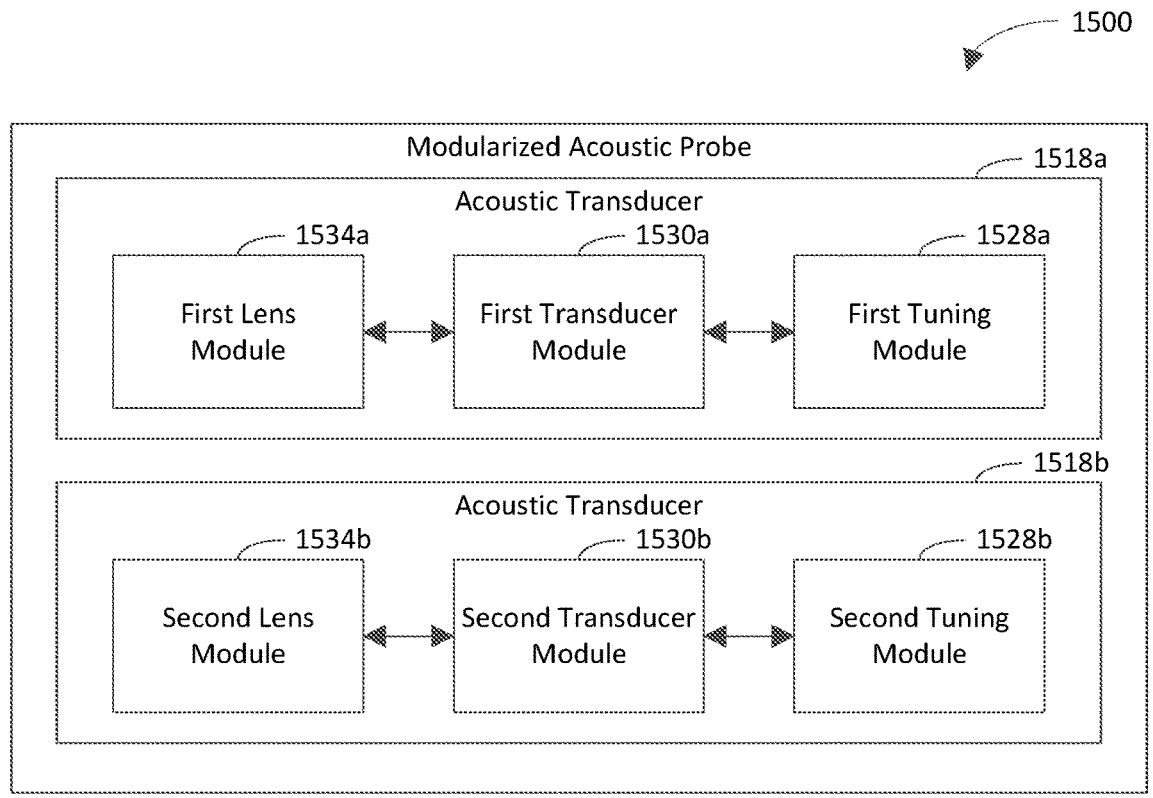
FIG. 15 illustrates an example modularized acoustic probe, including two acoustic transducers that are each capable of generating and detecting acoustic signals, in accordance with an embodiment.

FIG. 15 illustrates an example modularized acoustic probe 1500, including two acoustic transducers 1518a-1518b that are each capable of generating and detecting acoustic signals, in accordance with an embodiment. The first acoustic transducer 1518a includes a first lens module 1534*a*, a first transducer module 1530*a*, and a first tuning module 1528*a*. The second acoustic transducer 1518*b* includes a second lens module 1534*b*, a second transducer module 1530*b*, and a second tuning module 1528*b*. The first and second lens modules 1534*a*-1534*b* are operable in a manner similar to the lens module 234 shown in FIG. 2. The first and second transducer modules 1530*a*-1530*b* are operable in a manner similar to the transducer module 230 shown in FIG. 2. The first and second tuning modules 1528*a*-1528*b* are operable in a manner similar to the tuning module 228 shown in FIG. 2.

The acoustic designs of the respective first and second acoustic transducers 1518*a*-1518*b* may be same or different. For instance, although the first and second acoustic transducers 1518*a*-1518*b* include the same types of modules, the acoustic design of the first lens module 1534*a* may differ from the acoustic design of the second lens module 1534*b*; the acoustic design of the first transducer module 1530*a* may differ from the acoustic design of the second transducer module 1530*b*; and/or the acoustic design of the first tuning module 1528*a* may differ from the acoustic design of the second tuning module 1528*b*.

It will be recognized that even if the acoustic designs of the respective first and second acoustic transducers 1518*a*-1518*b* are the same, they can be inevitably different in one or more performance parameters due to natural variabilities in manufacturing processes. For example, the first acoustic transducer 1518*a* may be 2 dB more sensitive than the second acoustic transducer 1518*b*, or vice versa. In order to compensate for those transducer-to-transducer variations, the first and second tuning modules 1528*a*-1528*b* are designed with different settings to minimize the acoustic performance differences between the first and second acoustic transducers 1518*a*-1518*b*. For example, the first acoustic transducer 1518*a* may use 1.2 µH tuning inductors, and the second acoustic transducer 1518*b* may use 0.82 µH tuning inductors, or vice versa. Besides the tuning compensation approach, it is also possible to compensate for the variations with different settings in the imaging system (e.g., imaging system 104) to which the modularized acoustic probe 1500 is coupled. For example, the imaging system may apply a first gain to channels connected to transducer elements of the first acoustic transducer 1518*a* and a second gain, which is different form the first gain, to channels connected to transducer elements of the second acoustic transducer 1518*b* based on (e.g., according to) a difference between their sensitivities.

Figure 16:
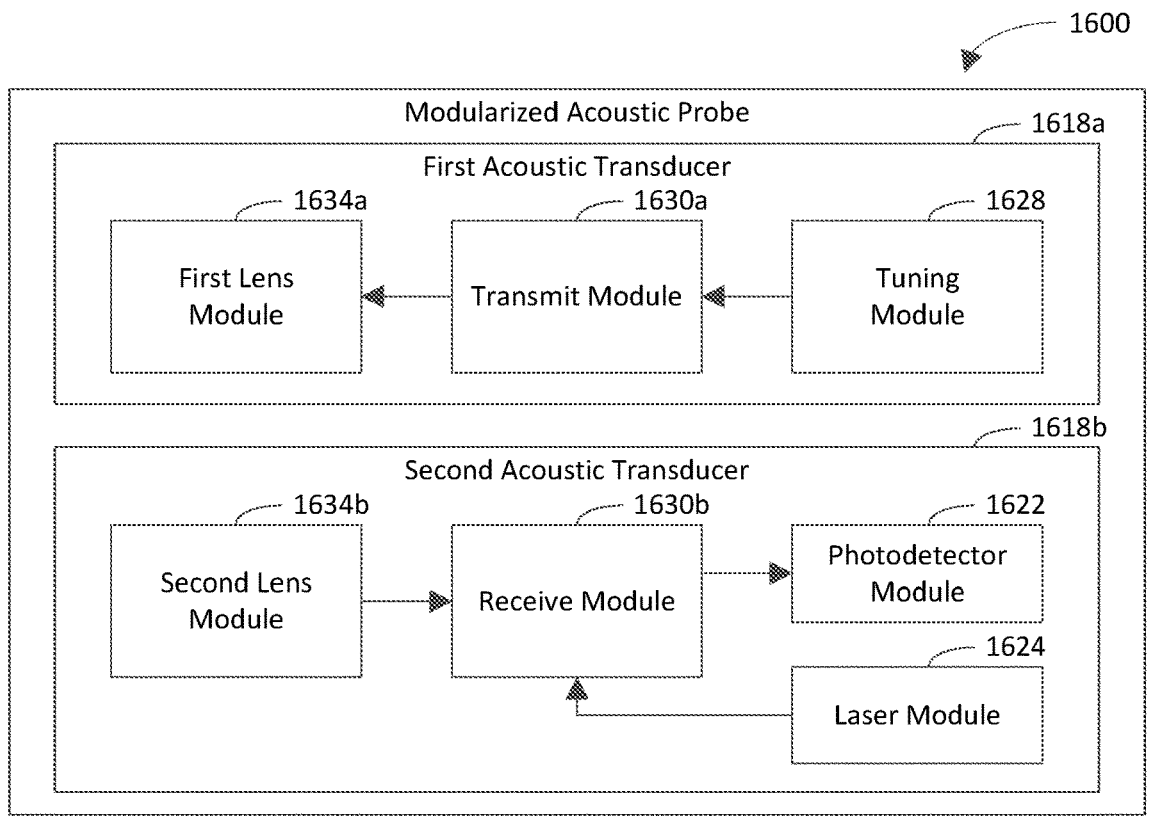
FIG. 16 illustrates an example modularized acoustic probe, including a first acoustic transducer configured to generate acoustic signals and a second acoustic transducer configured to detect acoustic signals, in accordance with an embodiment.

FIG. 16 illustrates an example modularized acoustic probe 1600, including a first acoustic transducer 1618*a* configured to generate acoustic signals and a second acoustic transducer 1618*b* configured to detect acoustic signals, in accordance with an embodiment. The first acoustic transducer 1618*a* is not configured to detect acoustic signals. For instance, the first acoustic transducer 1618*a* includes a first lens module 1634*a*, a transmit module 1630*a*, and a tuning module 1628. The transmit module 1630*a* is configured to generate acoustic signals and is not configured to detect acoustic signals. The transmit module 1630*a* may be made of any of the following sensors: PZT, single crystal, CMUT, and PMUT. The first lens module 1634*a* focuses the acoustic signals generated by the transmit module 1630*a*. The tuning module 1628 impedance matches transducer elements in the transmit module 1630*a* to an imaging system (e.g., imaging system 104) to which the modularized acoustic probe 1600 is coupled.

The second acoustic transducer 1618*b* is not configured to generate acoustic signals. For instance, the second acoustic transducer 1618*b* includes a second lens module 1634*b*, a receive module 1630*b*, a photodetector module 1622, and a laser module 1624. The receive module 1630*b* is configured to detect acoustic signals and is not configured to generate acoustic signals. The receive module 1630*b* is further configured to convert the detected acoustic signals to optical signals. For instance, the receive module 1630*a* may be made of optical sensors or other types of sensors. The second lens module 1634*b* focuses the acoustic signals received by the receive module 1630*b*. The laser module 1624 sends a laser beam to the receive module 1630*b* via optical fibers, a prism, or other structure to actuate the receive module 1630*b*. The photodetector module 1622 receives the laser beam modified by the acoustic signals from the receive module 1630*b* and converts the modified laser beam into electrical signals.

Figure 17:
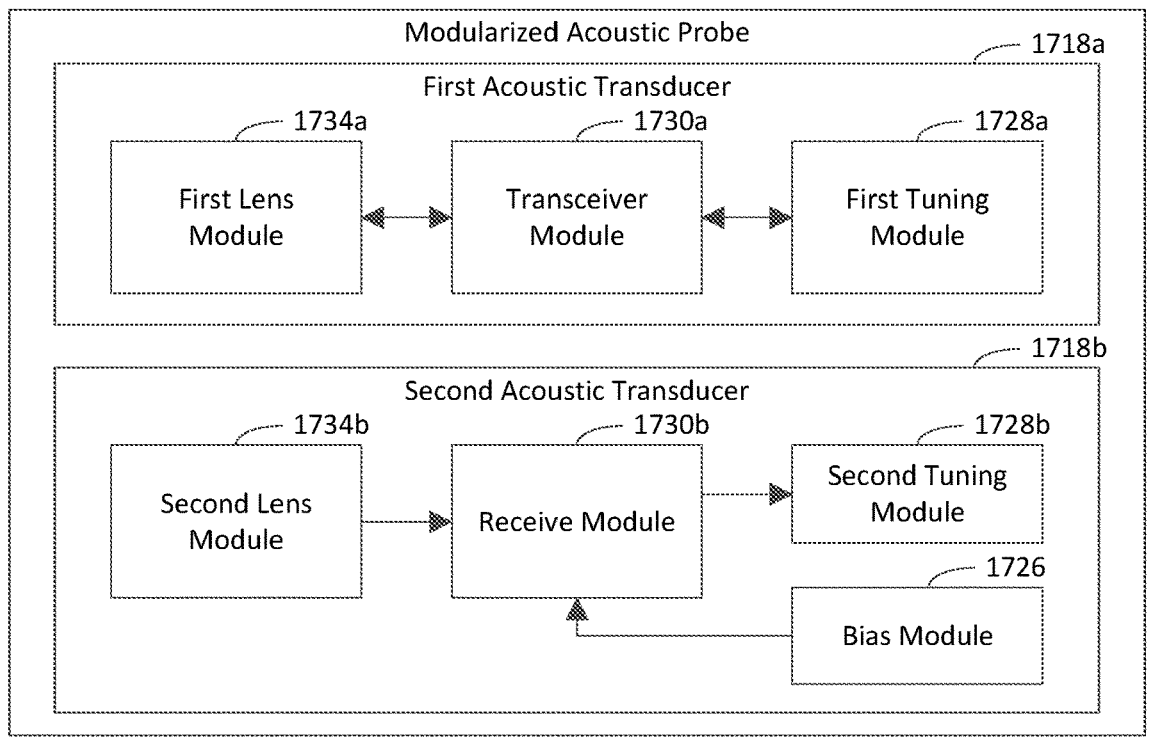
FIG. 17 illustrates an example modularized acoustic probe, including a first acoustic transducer configured to generate and detect acoustic signals and a second acoustic transducer configured to detect acoustic signals, in accordance with an embodiment.

FIG. 17 illustrates an example modularized acoustic probe 1700, including a first acoustic transducer 1718*a* configured to generate and detect acoustic signals and a second acoustic transducer 1718*b* configured to detect acoustic signals, in accordance with an embodiment. The first acoustic transducer 1718*a* includes a first lens module 1734*a*, a transceiver module 1730*a*, and a first tuning module 1728*a*, which are operable in a manner similar to the lens module 1534*a*, the first transducer module 1530*a*, and the first tuning module 1528*a*, respectively, shown in FIG. 15. The transceiver module 1730*a* may be made of any of the following types of sensors: PZT, single crystal, CMUT, and PMUT.

The second acoustic transducer 1718*b* is not configured to generate acoustic signals. The second acoustic transducer 1718*b* includes a second lens module 1734*b*, a receive module 1730*b*, a second tuning module 1728*b*, and a bias module 1726. The receive module 1730*b* is configured to detect acoustic signals and is not configured to generate acoustic signals. The second lens module 1734*b*, the second tuning module 1728*b*, and the bias module 1726 are operable in a manner similar to the lens module 234, the tuning module 228, and the bias module 232, respectively, shown in FIG. 2. The receive module 1730*b* may be made of any of the following types of sensors: PZT, single crystal, CMUT, PMUT, and optical sensors.

Figure 18:
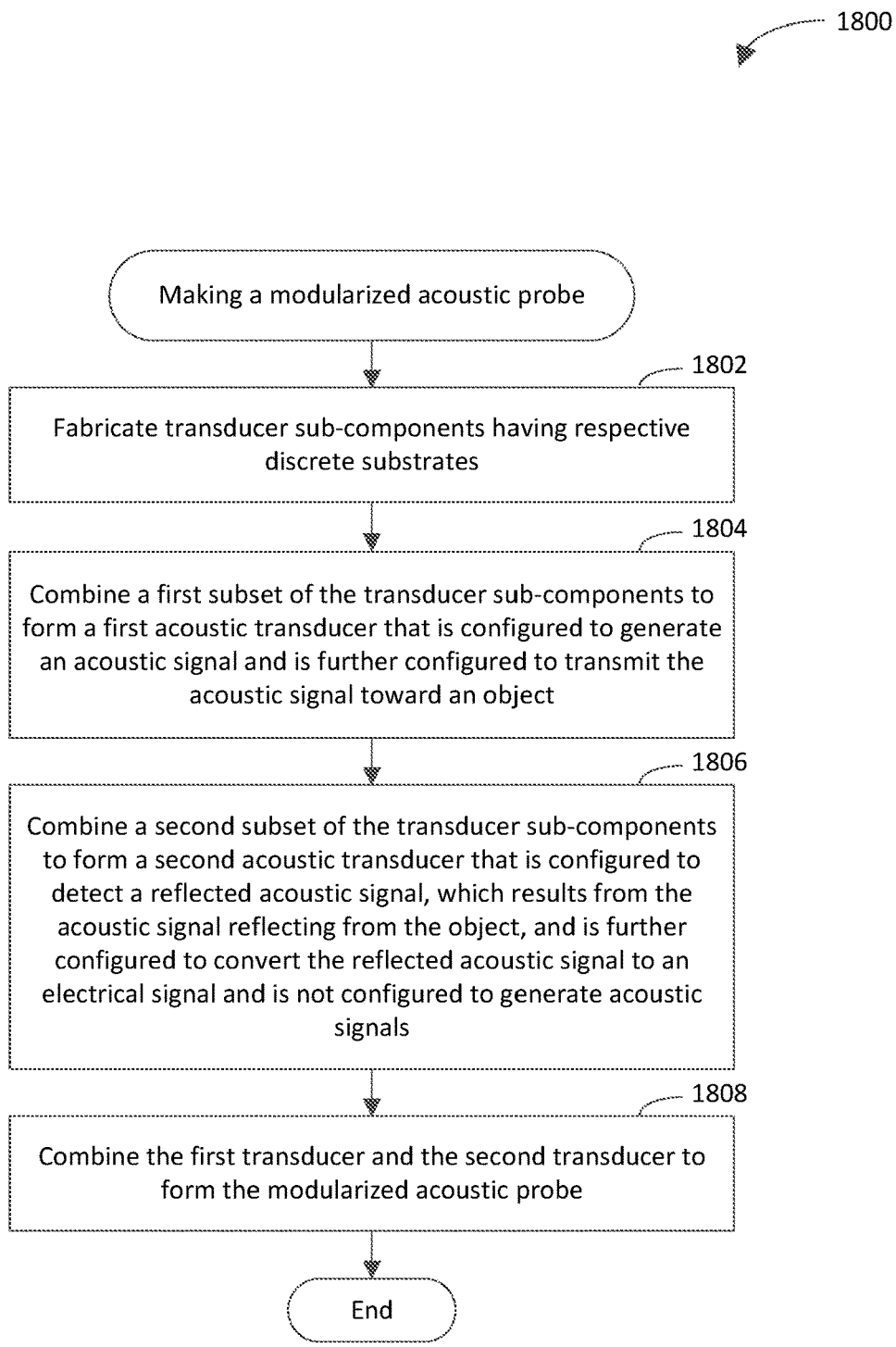
FIGS. 18-19 depict flowcharts of example methods for making a modularized acoustic probe in accordance with embodiments.
Figure 19:
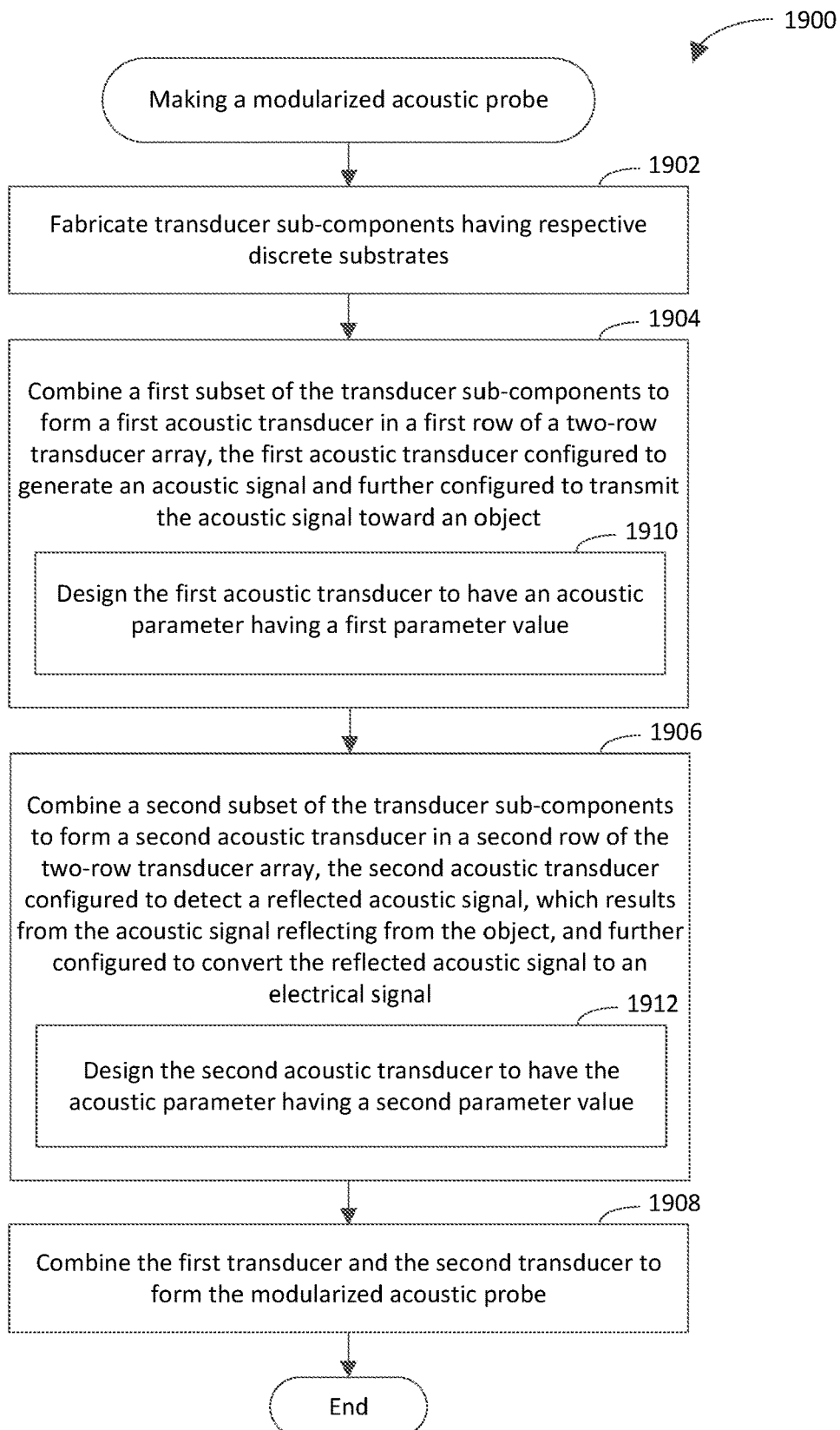
Figure 20:
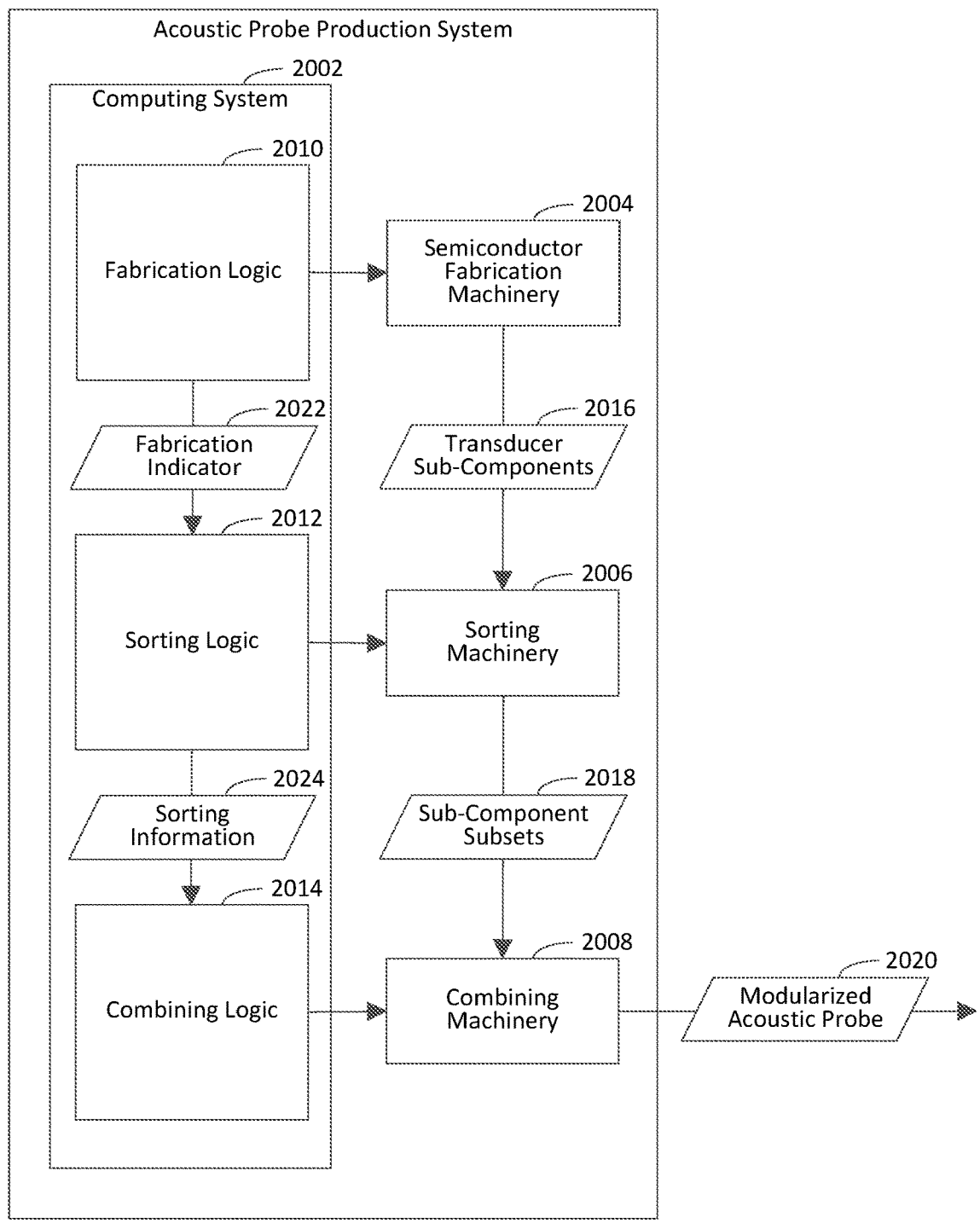
FIG. 20 is a block diagram of an example acoustic probe production system in accordance with an embodiment.

FIGS. 18-19 depict flowcharts 1800 and 1900 of example methods for making a modularized acoustic probe in accordance with embodiments. The flowcharts 1800 and 1900 may be performed by an acoustic probe production system 2000 shown in FIG. 20, for example. For illustrative purposes, the flowcharts 1800 and 1900 are described with respect to the acoustic probe production system 2000. The acoustic probe production system 2000 includes a computing system 2002, semiconductor fabrication machinery 2004, sorting machinery 2006, and combining machinery 2008. The computing system 2002 includes fabrication logic 2010, sorting logic 2012, and combining logic 2014. Further structural and operational embodiments will be apparent to persons skilled in the relevant art(s) based on the discussion regarding the flowcharts 1800 and 1900.

As shown in FIG. 18, the method of flowchart 1800 begins at step 1802. In step 1802, transducer sub-components having respective discrete substrates are fabricated. Each of the transducer sub-components may be a module (e.g., photodetector module 222, laser module 224, bias module 226, tuning module 228, transducer module 230, thermal module 232, or lens module 234) or a portion of a module (e.g., a transducer element or a transducer sub-element). In an example implementation, the semiconductor fabrication machinery 2004 fabricates transducer sub-components 2016 having respective discrete substrates. For example, the semiconductor fabrication machinery 2004 may fabricate the transducer sub-components 2016 based on instructions that are received from the fabrication logic 2010. In accordance with this example, the fabrication logic 2010 may be configured (e.g., programmed) to control the semiconductor fabrication machinery 2004 to perform processing steps (e.g., semiconductor processing steps) to fabricate the transducer sub-components 2016. Examples of such processing steps include but are not limited to surface passivation, photolithography, ion implantation, etching, plasma ashing, thermal treatments, chemical vapor deposition (CVD), atomic layer deposition (ALD), physical vapor deposition (PVD), molecular beam epitaxy (MBE), and die cutting. The fabrication logic 2010 may generate a fabrication indicator 2022 to indicate that the transducer sub-components 2016 have been fabricated.

At step 1804, a first subset of the transducer sub-components is combined to form a first acoustic transducer that is configured to generate an acoustic signal and is further configured to transmit the acoustic signal toward an object. Combining may include gluing, placing in contact, electrically coupling (e.g., soldering or connecting with an electrical connector), and/or optically coupling. In an example implementation, the combining machinery 2008 combines a first subset of the transducer sub-components 2016 to form the first acoustic transducer, which is configured to generate the acoustic signal and which is further configured to transmit the acoustic signal toward an object. For example, the combining machinery 2008 may combine the first subset of the transducer sub-components 2016 to form the first acoustic transducer based on instructions that are received from the combining logic 2014. In accordance with this example, the combining logic 2014 may be configured to control the combining machinery 2008 to combine the first subset of the transducer sub-components 2016 to form the first acoustic transducer.

In a sorting aspect of this implementation, the sorting machinery 2006 sorts the transducer sub-components 2016 into sub-component subsets 2018 that correspond to respective acoustic transducers. For instance, the sorting machinery 2006 may sort the transducer sub-components 2016 into the sub-component subsets 2018 based on instructions that are received from the sorting logic 2012. The sorting logic 2012 may be configured to control the sorting machinery 2006 to sort the transducer sub-components 2016 into the sub-component subsets 2018. For instance, the sorting machinery 2006 may control the sorting machinery 2006 to sort the transducer sub-components 2016 into the sub-component subsets 2018 based on receipt of the fabrication indicator 2022. The sorting logic may generate sorting information 2024 to indicate which of the transducer sub-components 2016 are included in each of the sub-component subsets 2018. In accordance with this aspect, the combining logic 2014 may be configured to control the combining machinery 2008 to combine the first subset of the transducer sub-components 2016 to form the first acoustic transducer based on the sorting information 2024 indicating which of the transducer sub-components 2016 are included in the first subset.

At step 1806, a second subset of the transducer sub-components is combined to form a second acoustic transducer that is configured to detect a reflected acoustic signal, which results from the acoustic signal reflecting from the object, and is further configured to convert the reflected acoustic signal to an electrical signal and is not configured to generate acoustic signals. The first subset of the transducer sub-components and the second subset of the transducer sub-components may include one or more common (e.g., same) transducer sub-components, or the first and second subsets may be mutually exclusive. In an example implementation, the combining machinery 2008 combines a second subset of the transducer sub-components 2016 to form the second acoustic transducer, which is configured to detect the reflected acoustic signal and which is further configured to convert the reflected acoustic signal to the electrical signal and is not configured to generate acoustic signals. For example, the combining machinery 2008 may combine the second subset of the transducer sub-components 2016 to form the second acoustic transducer based on instructions that are received from the combining logic 2014. In accordance with this example, the combining logic 2014 may be configured to control the combining machinery 2008 to combine the second subset of the transducer sub-components 2016 to form the second acoustic transducer.

In a sorting aspect of this implementation, the combining logic 2014 may be configured to control the combining machinery 2008 to combine the second subset of the transducer sub-components 2016 to form the second acoustic transducer based on the sorting information 2024 indicating which of the transducer sub-components 2016 are included in the second subset.

At step 1808, the first transducer and the second transducer are combined to form the modularized acoustic probe. In an example implementation, the combining machinery 2008 combines the first transducer and the second transducer to form a modularized acoustic probe 2020. For example, the combining machinery 2008 may combine the first transducer and the second transducer to form the modularized acoustic probe 2020 based on instructions that are received from the combining logic 2014. In accordance with this example, the combining logic 2014 may be configured to control the combining machinery 2008 to combine the first transducer and the second transducer to form the modularized acoustic probe 2020.

In some example embodiments, one or more steps 1802, 1804, 1806, and/or 1808 of flowchart 1800 may not be performed. Moreover, steps in addition to or in lieu of steps 1802, 1804, 1806, and/or 1808 may be performed. For instance, in an example embodiment, the flowchart of FIG. 1800 further includes testing the transducer sub-components. For example, each of the transducer sub-components may be individually tested to determine whether the respective transducer sub-component is to be discarded. In accordance with this example, each transducer sub-component that does not satisfy designated testing criteria may be discarded. In accordance with this embodiment, steps 1804, 1806, and 1808 may be performed in response to (e.g., following) the testing of the transducer sub-components. In an example implementation, the semiconductor fabrication machinery 2004 tests the transducer sub-components 2016.

In another example embodiment, the method of flowchart 1800 further includes acoustically testing the modularized acoustic probe. For instance, the modularized acoustic probe may be acoustically tested in response to performance of step 1808. In an example implementation, the combining machinery 2008 acoustically tests the modularized acoustic probe 2020.

In yet another example embodiment, the method of flowchart 1800 further includes connecting the modularized acoustic probe to an imaging system (e.g., imaging system 104) to generate acoustic (e.g., ultrasound) images. In an example implementation, the combining machinery 2008 connects the modularized acoustic probe 2020 to the imaging system.

As shown in FIG. 19, the method of flowchart 1900 begins at step 1902. In step 1902, transducer sub-components having respective discrete substrates are fabricated. In an example implementation, the semiconductor fabrication machinery 2004 fabricates transducer sub-components 2016 having respective discrete substrates. For example, the semiconductor fabrication machinery 2004 may fabricate the transducer sub-components 2016 based on instructions that are received from the fabrication logic 2010. The fabrication logic 2010 may generate a fabrication indicator 2022 to indicate that the transducer sub-components 2016 have been fabricated.

At step 1904, a first subset of the transducer sub-components is combined to form a first acoustic transducer in a first row of a two-row transducer array. The first acoustic transducer is configured to generate an acoustic signal and further configured to transmit the acoustic signal toward an object. In an example implementation, the combining machinery 2008 combines a first subset of the transducer sub-components 2016 to form the first acoustic transducer in the first row of the two-row transducer array. For example, the combining machinery 2008 may combine the first subset of the transducer sub-components 2016 to form the first acoustic transducer in the first row of the two-row transducer array based on instructions that are received from the combining logic 2014.

As mentioned above with reference to flowchart 1800 of FIG. 18, the sorting machinery 2006 may sort the transducer sub-components 2016 into sub-component subsets 2018 that correspond to respective acoustic transducers. For instance, the sorting machinery 2006 may sort the transducer sub-components 2016 into the sub-component subsets 2018 based on instructions that are received from the sorting logic 2012. The sorting logic 2012 may be configured to control the sorting machinery 2006 to sort the transducer sub-components 2016 into the sub-component subsets 2018. For instance, the sorting machinery 2006 may control the sorting machinery 2006 to sort the transducer sub-components 2016 into the sub-component subsets 2018 based on receipt of the fabrication indicator 2022. The sorting logic may generate sorting information 2024 to indicate which of the transducer sub-components 2016 are included in each of the sub-component subsets 2018. In accordance with this aspect, the combining logic 2014 may be configured to control the combining machinery 2008 to combine the first subset of the transducer sub-components 2016 to form the first acoustic transducer in the first row of the two-row transducer array based on the sorting information 2024 indicating which of the transducer sub-components 2016 are included in the first subset.

Step 1904 includes step 1910. At step 1910, the first acoustic transducer is designed to have an acoustic parameter having a first parameter value. For example, the combining machinery 2008 may design the first acoustic transducer to have the acoustic parameter having the first parameter value. In accordance with this example, the combining machinery 2008 may combine the first subset of the transducer sub-components 2016 to form the first acoustic transducer based on the sorting machinery 2006 selecting the transducer sub-components in the first subset based a determination that the transducer sub-components in the first subset, when combined, will provide the acoustic parameter having the first parameter value. For instance, the sorting logic 2012 may select which transducer sub-components are to be included in the first subset based on test information regarding the transducer sub-components 2016. The sorting logic 2012 may determine which combination of transducer sub-components will provide the acoustic parameter having the first parameter value based on an analysis of the test information.

At step 1906, a second subset of the transducer sub-components is combined to form a second acoustic transducer in a second row of the two-row transducer array. The second acoustic transducer is configured to detect a reflected acoustic signal, which results from the acoustic signal reflecting from the object, and further configured to convert the reflected acoustic signal to an electrical signal. The first subset of the transducer sub-components and the second subset of the transducer sub-components may include one or more common (e.g., same) transducer sub-components, or the first and second subsets may be mutually exclusive. In an example implementation, the combining machinery 2008 combines a second subset of the transducer sub-components 2016 to form the second acoustic transducer in the second row of the two-row transducer array. For example, the combining machinery 2008 may combine the second subset of the transducer sub-components 2016 to form the second acoustic transducer in the second row of the two-row transducer array based on instructions that are received from the combining logic 2014.

In a sorting aspect of this implementation, the combining logic 2014 may be configured to control the combining machinery 2008 to combine the second subset of the transducer sub-components 2016 to form the second acoustic transducer in the second row of the two-row transducer array based on the sorting information 2024 indicating which of the transducer sub-components 2016 are included in the second sub set.

Step 1906 includes step 1912. At step 1912, the second acoustic transducer is designed to have the acoustic parameter having a second parameter value. For example, the combining machinery 2008 may design the second acoustic transducer to have the acoustic parameter having the second parameter value. In accordance with this example, the combining machinery 2008 may combine the second subset of the transducer sub-components 2016 to form the second acoustic transducer based on the sorting machinery 2006 selecting the transducer sub-components in the second subset based a determination that the transducer sub-components in the second subset, when combined, will provide the acoustic parameter having the second parameter value. For instance, the sorting logic 2012 may select which transducer sub-components are to be included in the second subset based on test information regarding the transducer sub-components 2016. The sorting logic 2012 may determine which combination of transducer sub-components will provide the acoustic parameter having the second parameter value based on the analysis of the test information.

At step 1908, the first transducer and the second transducer are combined to form the modularized acoustic probe. In an example implementation, the combining machinery 2008 combines the first transducer and the second transducer to form the modularized acoustic probe 2020. For example, the combining machinery 2008 may combine the first transducer and the second transducer to form the modularized acoustic probe 2020 based on instructions that are received from the combining logic 2014.

In some example embodiments, one or more steps 1902, 1904, 1906, 1908, 1910, and/or 1912 of flowchart 1900 may not be performed. Moreover, steps in addition to or in lieu of steps 1902, 1904, 1906, 1908, 1910, and/or 1912 may be performed. For instance, in an example embodiment, the flowchart of FIG. 1900 further includes testing the transducer sub-components. For example, each of the transducer sub-components may be individually tested to determine whether the respective transducer sub-component is to be discarded. In accordance with this example, each transducer sub-component that does not satisfy designated testing criteria may be discarded. In accordance with this embodiment, steps 1904, 1906, 1908, 1910, and 1912 may be performed in response to (e.g., following) the testing of the transducer sub-components. In an example implementation, the semiconductor fabrication machinery 2004 tests the transducer sub-components 2016.

In another example embodiment, the method of flowchart 1900 further includes acoustically testing the modularized acoustic probe. For instance, the modularized acoustic probe may be acoustically tested in response to performance of step 1908. In an example implementation, the combining machinery 2008 acoustically tests the modularized acoustic probe 2020.

In yet another example embodiment, the method of flowchart 1900 further includes connecting the modularized acoustic probe to an imaging system (e.g., imaging system 104) to generate acoustic (e.g., ultrasound) images. In an example implementation, the combining machinery 2008 connects the modularized acoustic probe 2020 to the imaging system.

It will be recognized that the acoustic probe production system 2000 may not include one or more of the computing system 2002, the semiconductor fabrication machinery 2004, the sorting machinery 2006, the combining machinery 2008, the fabrication logic 2010, the sorting logic 2012, and/or the combining logic 2014. Furthermore, the acoustic probe production system 2000 may include components in addition to or in lieu of the computing system 2002, the semiconductor fabrication machinery 2004, the sorting machinery 2006, the combining machinery 2008, the fabrication logic 2010, the sorting logic 2012, and/or the combining logic 2014.

Any one or more of the fabrication logic 2010, the sorting logic 2012, the combining logic 2014, flowchart 1800, and/or flowchart 1900 may be implemented in hardware, software, firmware, or any combination thereof.

For example, any one or more of the fabrication logic 2010, the sorting logic 2012, the combining logic 2014, flowchart 1800, and/or flowchart 1900 may be implemented, at least in part, as computer program code configured to be executed in one or more processors.

In another example, any one or more of the fabrication logic 2010, the sorting logic 2012, the combining logic 2014, flowchart 1800, and/or flowchart 1900 may be implemented, at least in part, as hardware logic/electrical circuitry. Such hardware logic/electrical circuitry may include one or more hardware logic components. Examples of a hardware logic component include but are not limited to a field-programmable gate array (FPGA), an application-specific integrated circuit (ASIC), an application-specific standard product (ASSP), a system-on-a-chip system (SoC), a complex programmable logic device (CPLD), etc. For instance, a SoC may include an integrated circuit chip that includes one or more of a processor (e.g., a microcontroller, microprocessor, digital signal processor (DSP), etc.), memory, one or more communication interfaces, and/or further circuits and/or embedded firmware to perform its functions.

III. Further Discussion of Some Example Embodiments (A1) An example modularized acoustic probe (FIG. 1, 102; FIG. 3, 300, FIG. 16, 1600; FIG. 17, 1700) comprises a first acoustic transducer (FIG. 3, 318*a*, FIG. 16, 1618*a*; FIG. 17, 1718*a*) configured to generate an acoustic signal (FIG. 3, 344) and to transmit the acoustic signal toward an object (FIG. 3, 348); and a second acoustic transducer (FIG. 3, 318*b*, FIG. 16, 1618*b*; FIG. 17, 1718*b*) configured to detect a reflected acoustic signal (FIG. 3, 346), which results from the acoustic signal reflecting from the object, and to convert the reflected acoustic signal to an electrical signal. The second acoustic transducer is not configured to generate acoustic signals. The first acoustic transducer and the second acoustic transducer have respective discrete substrates (FIGS. 3, 342*a* and 3432*b*).

(A2) In the example modularized acoustic probe of A1, wherein the second acoustic transducer comprises: an acousto-optic sensor configured to convert the reflected acoustic signal to an optical signal; a laser configured to generate a laser beam to actuate the acousto-optic sensor; and a photodetector configured to detect the laser modulated by the reflected acoustic signal.

(A3) In the example modularized acoustic probe of any of A1-A2, wherein the second acoustic transducer further comprises a plurality of whispering gallery mode (WGM) resonators configured to modulate the laser beam.

(A4) In the example modularized acoustic probe of any of A1-A3, wherein the second acoustic transducer is not capable of generating the acoustic signals.

(A5) In the example modularized acoustic probe of any of A1-A4, wherein the first acoustic transducer is further configured to convert the reflected acoustic signal to a second electrical signal.

(A6) In the example modularized acoustic probe of any of A1-A5, wherein the first acoustic transducer has a first type of transducer structure; and wherein the second acoustic transducer has a second type of transducer structure that is different from the first type of transducer structure.

(A7) In the example modularized acoustic probe of any of A1-A6, comprising: a first array of first acoustic transducers, a second array of second acoustic transducers, and a third array of third acoustic transducers. Each first acoustic transducer in the first array is configured to generate a respective acoustic signal and to transmit the respective acoustic signal toward the object. Each second acoustic transducer in the second array is configured to detect reflected acoustic signals, which result from the respective acoustic signals reflecting from the object, and to convert the reflected acoustic signals to a respective electrical signal. Each third acoustic transducer in the third array is configured to at least one of generate a respective acoustic signal or convert the reflected acoustic signals to an electrical signal.

(A8) In the example modularized acoustic probe of any of A1-A7, wherein each of the first array, the second array, and the third array is a curvilinear array, each curvilinear array having a curved shape.

(A9) In the example modularized acoustic probe of any of A1-A8, comprising: a first number of first acoustic transducers and a second number of second acoustic transducers. Each first acoustic transducer is configured to generate a respective acoustic signal and to transmit the respective acoustic signal toward the object. Each second acoustic transducer is configured to detect reflected acoustic signals, which result from the respective acoustic signals reflecting from the object, and to convert the reflected acoustic signals to a respective electrical signal. Each first acoustic transducer and each second acoustic transducer has a respective discrete substrate. The first number and the second number are not same.

(A10) In the example modularized acoustic probe of any of A1-A9, wherein the modularized acoustic probe is in a shape of a disk; wherein the first acoustic transducer forms a first portion of the disk; and wherein the second acoustic transducer forms a second portion of the disk.

(A11) In the example modularized acoustic probe of any of A1-A10, wherein the first acoustic transducer forms a ring around the second acoustic transducer; or wherein the second acoustic transducer forms a ring around the first acoustic transducer.

(B1) An example modularized acoustic probe (FIG. 1, 102; FIG. 3, 300, FIG. 16, 1600; FIG. 17, 1700) comprises a first acoustic transducer (FIG. 3, 318*a*, FIG. 15, 1518*a*; FIG. 16, 1618*a*; FIG. 17, 1718*a*) in a first row of a two-row transducer array and a second acoustic transducer (FIG. 3, 318*b*, FIG. 15, 1518*b*; FIG. 16, 1618*b*; FIG. 17, 1718*b*) in a second row of the two-row transducer array. The first acoustic transducer is configured to generate an acoustic signal (FIG. 3, 344) and to transmit the acoustic signal toward an object (FIG. 3, 348). The second acoustic transducer is configured to detect a reflected acoustic signal (FIG. 3, 346), which results from the acoustic signal reflecting from the object, and to convert the reflected acoustic signal to an electrical signal. The first acoustic transducer and the second acoustic transducer have respective discrete substrates (FIGS. 3, 342*a* and 3432*b*). The first acoustic transducer is designed to have an acoustic parameter having a first parameter value, and the second acoustic transducer is designed to have the acoustic parameter having a second parameter value that is different from the first parameter value.

(B2) In the example modularized acoustic probe of B1, wherein the second acoustic transducer is not configured to generate acoustic signals.

(B3) In the example modularized acoustic probe of any of B1-B2, wherein the second acoustic transducer is not capable of generating acoustic signals.

(B4) In the example modularized acoustic probe of any of B1-B3, wherein the second acoustic transducer comprises: an acousto-optic sensor configured to convert the reflected acoustic signal to an optical signal; a laser configured to generate a laser beam to actuate the acousto-optic sensor; and a photodetector configured to detect the laser modulated by the reflected acoustic signal.

(B5) In the example modularized acoustic probe of any of B1-B4, wherein the second acoustic transducer further comprises a plurality of whispering gallery mode (WGM) resonators configured to modulate the laser beam.

(B6) In the example modularized acoustic probe of any of B1-B5, wherein the first acoustic transducer is further configured to convert the reflected acoustic signal to a second electrical signal.

(B7) In the example modularized acoustic probe of any of B1-B6, wherein the first acoustic transducer has a first type of transducer structure; and wherein the second acoustic transducer has a second type of transducer structure that is different from the first type of transducer structure.

(B8) In the example modularized acoustic probe of any of B1-B7, wherein the first row of the two-row transducer array comprises a first number of first acoustic transducers and wherein the second row of the two-row transducer array comprises a second number of second acoustic transducers. Each first acoustic transducer is configured to generate a respective acoustic signal and to transmit the respective acoustic signal toward the object. Each second acoustic transducer is configured to detect reflected acoustic signals, which result from the respective acoustic signals reflecting from the object, and to convert the reflected acoustic signals to a respective electrical signal. Each first acoustic transducer and each second acoustic transducer has a respective discrete substrate. The first number and the second number are not same.

(B9) In the example modularized acoustic probe of any of B1-B8, wherein the modularized acoustic probe includes a transducer combination in a shape of a disk; wherein the transducer combination includes the first acoustic transducer and the second acoustic transducer; wherein the first acoustic transducer forms a first portion of the disk; and wherein the second acoustic transducer forms a second portion of the disk.

(C1) A method of making a modularized acoustic probe (FIG. 1, 102; FIG. 3, 300, FIG. 16, 1600; FIG. 17, 1700) comprises: fabricating (FIG. 18, 1802) a plurality of transducer sub-components (FIG. 20, 2004) having a plurality of respective discrete substrates; combining (FIG. 18, 1804) a first subset of the plurality of transducer sub-components to form a first acoustic transducer (FIG. 3, 318*a*, FIG. 16, 1618*a*; FIG. 17, 1718*a*) that is configured to generate an acoustic signal (FIG. 3, 344) and is further configured to transmit the acoustic signal toward an object (FIG. 3, 348); combining (FIG. 18, 1806) a second subset of the plurality of transducer sub-components to form a second acoustic transducer (FIG. 3, 318*b*, FIG. 16, 1618*b*; FIG. 17, 1718*b*) that is configured to detect a reflected acoustic signal (FIG. 3, 346), which results from the acoustic signal reflecting from the object, and is further configured to convert the reflected acoustic signal to an electrical signal and is not configured to generate acoustic signals; and combining (FIG. 18, 1808) the first transducer and the second transducer to form the modularized acoustic probe.

(D1) A method of making a modularized acoustic probe (FIG. 1, 102; FIG. 3, 300, FIG. 15, 1500; FIG. 16, 1600; FIG. 17, 1700) comprises: fabricating (FIG. 19, 1902) a plurality of transducer sub-components (FIG. 20, 2004) having a plurality of respective discrete substrates; combining (FIG. 19, 1904) a first subset of the plurality of transducer sub-components to form a first acoustic transducer (FIG. 3, 318*a*, FIG. 15, 1518*a*; FIG. 16, 1618*a*; FIG. 17, 1718*a*) in a first row of a two-row transducer array, the first acoustic transducer configured to generate an acoustic signal (FIG. 3, 344) and further configured to transmit the acoustic signal toward an object (FIG. 3, 348), wherein combining the first subset of the plurality of transducer sub-components comprises designing (FIG. 19, 1910) the first acoustic transducer to have an acoustic parameter having a first parameter value; combining (FIG. 19, 1906) a second subset of the plurality of transducer subcomponents to form a second acoustic transducer (FIG. 3, 318*b*, FIG. 15, 1518*b*; FIG. 16, 1618*b*; FIG. 17, 1718*b*) in a second row of the two-row transducer array, the second acoustic transducer configured to detect a reflected acoustic signal (FIG. 3, 346), which results from the acoustic signal reflecting from the object, and further configured to convert the reflected acoustic signal to an electrical signal, wherein combining the second subset of the plurality of transducer sub-components comprises designing (FIG. 19, 1912) the second acoustic transducer to have the acoustic parameter having a second parameter value that is different from the first parameter value; and combining (FIG. 19, 1908) the first transducer and the second transducer to form the modularized acoustic probe.

IV. Example Computer System

Figure 21:
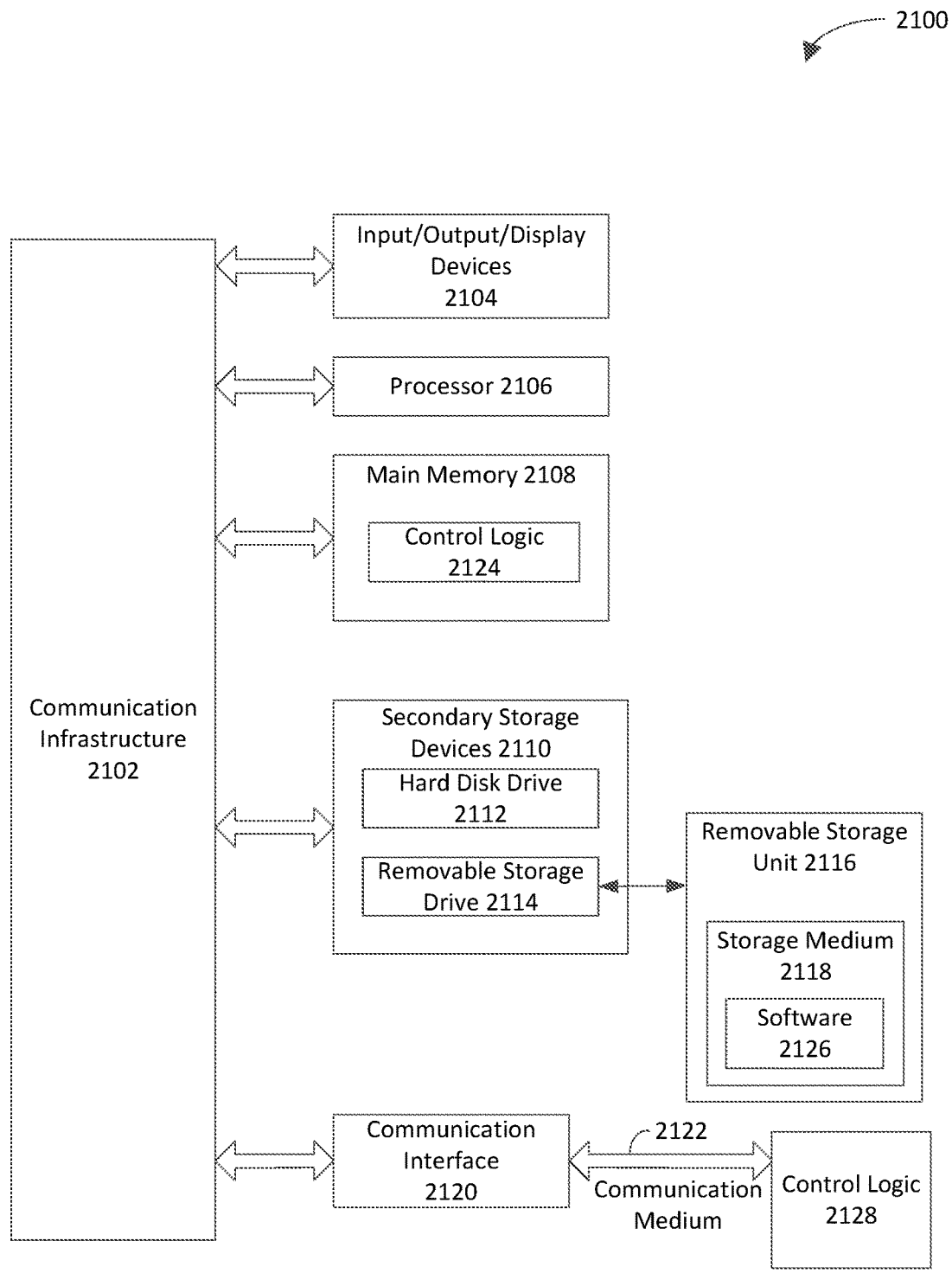
FIG. 21 is an example implementation of a computing system shown in FIG. 1 or 19 in accordance with an embodiment.

Example embodiments, systems, components, subcomponents, devices, methods, flowcharts, steps, and/or the like described herein, including but not limited to the acoustic system 100, the acoustic probe production system 2000, flowchart 1800, and flowchart 1900, may be implemented in hardware (e.g., hardware logic/electrical circuitry), or any combination of hardware with software (computer program code configured to be executed in one or more processors or processing devices) and/or firmware. The embodiments described herein, including systems, methods/processes, and/or apparatuses, may be implemented using well known computing devices, such as computer 2100 shown in FIG. 21. For example, the acoustic system 100, the acoustic probe production system 2000, each of the steps of flowchart 1800, and each of the steps of flowchart 1900 may be implemented using one or more computers 2100.

The computer 2100 can be any commercially available and well known communication device, processing device, and/or computer capable of performing the functions described herein, such as devices/computers available from Microsoft Corporation, HP, Inc., Lenovo Group Limited, International Business Machines Corporation, Apple Inc., Dell Technologies Inc., Cray Inc., Samsung Electronics America, Inc., etc. The computer 2100 may be any type of computer, including a server, a desktop computer, a laptop computer, a tablet computer, a wearable computer such as a smart watch or a head-mounted computer, a personal digital assistant, a cellular telephone, etc.

The computer 2100 includes one or more processors (also called central processing units, or CPUs), such as a processor 2106. The processor 2106 is connected to a communication infrastructure 2102, such as a communication bus. In some embodiments, the processor 2106 can simultaneously operate multiple computing threads. The computer 2100 also includes a primary or main memory 2108, such as random access memory (RAM). The main memory 2108 stores control logic 2124 (e.g., computer software or firmware) and data.

The computer 2100 also includes one or more secondary storage devices 2110. The secondary storage devices 2110 include, for example, a hard disk drive 2112 and/or a removable storage device or drive 2114, as well as other types of storage devices, such as memory cards and memory sticks. For instance, the computer 2100 may include an industry standard interface, such a universal serial bus (USB) interface for interfacing with devices such as a memory stick. The removable storage drive 2114 represents a floppy disk drive, a magnetic tape drive, a compact disk drive, an optical storage device, a tape backup, etc.

The removable storage drive 2114 interacts with a removable storage unit 2116. The removable storage unit 2116 includes a computer useable or readable storage medium 2118 that stores computer software 2126 (control logic) and/or data. The removable storage unit 2116 represents a floppy disk, magnetic tape, compact disk (CD), digital versatile disc (DVD), Blu-ray disc, optical storage disk, memory stick, memory card, or any other computer data storage device. The removable storage drive 2114 reads from and/or writes to the removable storage unit 2116 in a well-known manner.

The computer 2100 also includes input/output/display devices 2104, such as touchscreens, LED and LCD displays, keyboards, pointing devices, etc.

The computer 2100 further includes a communication or network interface 2120. The communication interface 2120 enables the computer 2100 to communicate with remote devices. For example, the communication interface 2120 allows the computer 2100 to communicate over communication networks or mediums 2122 (representing a form of a computer useable or readable medium), such as local area networks (LANs), wide area networks (WANs), the Internet, etc. The network interface 2120 may interface with remote sites or networks via wired or wireless connections. Examples of the communication interface 2120 include but are not limited to a modem (e.g., for 4G and/or 5G communication(s)), a network interface card (e.g., an Ethernet card for Wi-Fi and/or other protocols), a communication port, a Personal Computer Memory Card International Association (PCMCIA) card, a wired or wireless USB port, etc. Control logic 2128 may be transmitted to and from the computer 2100 via the communication medium 2122.

Any apparatus or manufacture comprising a computer useable or readable medium having control logic (e.g., software or firmware) stored therein is referred to herein as a computer program product or program storage device. Examples of a computer program product include but are not limited to main memory 2108, secondary storage devices 2110 (e.g., hard disk drive 2112), and removable storage unit 2116. Such computer program products, having control logic stored therein that, when executed by one or more data processing devices, cause such data processing devices to operate as described herein, represent embodiments. For example, such computer program products, when executed by the processor 2106, may cause the processor 2106 to perform any of the steps of flowchart 1800 of FIG. 18 and/or flowchart 1900 of FIG. 19.

Devices in which embodiments may be implemented may include storage, such as storage drives, memory devices, and further types of computer-readable media. Examples of such computer-readable storage media include a hard disk, a removable magnetic disk, a removable optical disk, flash memory cards, digital video disks, random access memories (RAMs), read only memories (ROM), and the like. As used herein, the terms "computer program medium" and "computer-readable medium" are used to generally refer to media (e.g., non-transitory media) such as the hard disk associated with a hard disk drive, a removable magnetic disk, a removable optical disk (e.g., CD ROMs, DVD ROMs, etc.), zip disks, tapes, magnetic storage devices, optical storage devices, MEMS-based storage devices, nanotechnology-based storage devices, as well as other media such as flash memory cards, digital video discs, RAM devices, ROM devices, and the like. A computer-readable storage medium is not a signal, such as a carrier signal or a propagating signal. For instance, a computer-readable storage medium may not include a signal. Accordingly, a computer-readable storage medium does not constitute a signal per se.

Such computer-readable storage media may store program modules that include computer program logic to implement, for example, embodiments, systems, components, subcomponents, devices, methods, flowcharts, steps, and/or the like described herein (as noted above), and/or further embodiments described herein. Embodiments are directed to computer program products comprising such logic (e.g., in the form of program code, instructions, or software) stored on any computer useable medium. Such program code, when executed in one or more processors, causes a device to operate as described herein.

Note that such computer-readable storage media are distinguished from and non-overlapping with communication media (do not include communication media). Communication media embodies computer-readable instructions, data structures, program modules or other data in a modulated data signal such as a carrier wave. The term "modulated data signal" means a signal that has one or more of its characteristics set or changed in such a manner as to encode information in the signal. By way of example, and not limitation, communication media includes wireless media such as acoustic, RF, infrared and other wireless media, as well as wired media. Embodiments are also directed to such communication media.

The disclosed technologies can be put into practice using software, firmware, and/or hardware implementations other than those described herein. Any software, firmware, and hardware implementations suitable for performing the functions described herein can be used.

V. Conclusion

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims, and other equivalent features and acts are intended to be within the scope of the claims.

What is claimed is:

1. A modularized acoustic probe comprising:
    a probe scanhead including:
        an acoustic transducer disposed on a first substrate and configured to generate an acoustic signal and to transmit the acoustic signal toward tissue or bone;
        an optical sensor disposed on a second substrate and configured to detect a reflected acoustic signal, which results from the acoustic signal reflecting from the tissue or bone and to convert the reflected acoustic signal to an electrical signal, wherein the first substrate of the acoustic transducer and the second substrate of the optical sensor are discrete substrates and wherein the acoustic transducer and the optical sensor have at least one different acoustic parameter;
        a thermal module disposed on the second substrate including at least one thermal circuit and configured to regulate a temperature inside the probe scanhead;
        a first lens module associated with the acoustic transducer and configured to provide mechanical focusing of acoustic signals transmitted by the acoustic transducer; and
        a second lens module associated with the optical sensor having a different acoustic design than the first lens module and configured to provide mechanical focusing of acoustic signals received by the optical sensor.

2. The modularized acoustic probe of claim 1, wherein the optical sensor comprises:
    an acousto-optic sensor configured to convert the reflected acoustic signal to an optical signal;
    a laser configured to generate a laser beam to actuate the acousto-optic sensor; and
    a photodetector configured to detect the laser beam modulated by the reflected acoustic signal.

3. The modularized acoustic probe of claim 2,
    wherein the optical sensor further comprises:
    a plurality of whispering gallery mode (WGM) resonators configured to modulate the laser beam.

4. The modularized acoustic probe of claim 1, wherein the acoustic transducer is further configured to convert the reflected acoustic signal to a second electrical signal.

5. The modularized acoustic probe of claim 1, comprising:
    a first array of acoustic transducers, each acoustic transducer in the first array configured to generate a respective acoustic signal and to transmit the respective acoustic signal toward the tissue or bone;
    a second array of optical sensors, each optical sensor in the second array configured to detect reflected acoustic signals reflecting from the tissue or bone, which result from the respective acoustic signals reflecting from the tissue or bone, and to convert the reflected acoustic signals to a respective electrical signal; and
    a third array of either optical sensors or acoustic transducers the third array configured to at least one of generate a respective acoustic signal or convert the reflected acoustic signals to respective electrical signals;
    each of the first array, the second array, and the third array having a respective discrete substrate.

6. The modularized acoustic probe of claim 5, wherein each of the first array, the second array, and the third array is a curvilinear array, each curvilinear array having a curved shape.

7. The modularized acoustic probe of claim 1, comprising:
    a first number of acoustic transducers, each acoustic transducer configured to generate a respective acoustic signal and to transmit the respective acoustic signal toward the tissue or bone; and
    a second number of optical sensors, each optical sensor configured to detect respective acoustic signals reflected from the bone or tissue, and to convert the respective acoustic signals to respective electrical signals;
    each acoustic transducer and each optical sensor having a respective discrete substrate; and
    the first number and the second number are not same.

8. The modularized acoustic probe of claim 1, wherein the modularized acoustic probe is in a shape of a disk;
    the acoustic transducer forming a first portion of the disk; and
    the optical sensor forming a second portion of the disk.

9. The modularized acoustic probe of claim 1,
    wherein the acoustic transducer is included in an acoustic transducer module forming a ring around the optical sensor; or
    wherein the optical sensor is included within an optical sensor module forming a ring around the acoustic transducer.

10. The modularized acoustic probe of claim 1, wherein the acoustic parameter includes at least one of the following:
   a center frequency;
   a resonant frequency;
   a dynamic range;
   a quality factor.

11. The modularized acoustic probe of claim 1, wherein:
   the acoustic parameter is a center frequency,
   the acoustic transducer has a first center frequency of X, and
   the optical sensor has a second center frequency of X*Y.

12. The modularized acoustic probe of claim 11, where X is a number selected from 3 MHZ, 3.5 MHZ, 6 MHz, or 7.5 MHz, and Y is a number selected from 2, 12/7, 15/7, 2.5, or 3.

13. The modularized acoustic probe of claim 1, wherein:
   the acoustic transducer is a part of a first row of acoustic transducers,
   the optical sensor is a part of a second row of optical sensors,
   the modularized acoustic probe includes a third row of acoustic transducers, and
   each of the first row of acoustic transducers, the second row of optical sensors, and the third row of acoustic transducers have respective discrete substrates and at least one different acoustic parameter.

14. The modularized acoustic probe of claim 1, wherein:
   the acoustic transducer is configured not to detect acoustic signals, and
   the optical sensor is configured not to generate acoustic signals.

15. A modularized acoustic probe comprising:
   a probe scanhead including:
   an acoustic transducer disposed on a first substrate and in a first row of a two-row transducer array, the acoustic transducer configured to generate an acoustic signal and to transmit the acoustic signal toward tissue or bone;
   an optical sensor disposed on a second substrate and in a second row of the two-row transducer array, the optical sensor configured to detect a reflected acoustic signal, which results from the acoustic signal reflecting from the tissue or bone, and to convert the reflected acoustic signal to an electrical signal, wherein the first substrate of the acoustic transducer and the second substrate of the optical sensor are discrete substrates, and wherein the acoustic transducer and the optical sensor have at least one different acoustic parameter;
   a thermal module disposed on the second substrate including at least one thermal circuit and configured to regulate a temperature inside the probe scanhead;
   a first lens module associated with the acoustic transducer and configured to provide mechanical focusing of acoustic signals transmitted by the acoustic transducer; and
   a second lens module associated with the optical sensor having a different acoustic design than the first lens module and configured to provide mechanical focusing of acoustic signals received by the optical sensor.

16. The modularized acoustic probe of claim 15, wherein the optical sensor comprises:
   an acousto-optic sensor configured to convert the reflected acoustic signal to an optical signal;
   a laser configured to generate a laser beam to actuate the acousto-optic sensor; and
   a photodetector configured to detect the laser beam modulated by the reflected acoustic signal.

17. The modularized acoustic probe of claim 16, wherein the optical sensor further comprises:
   a plurality of whispering gallery mode (WGM) resonators configured to modulate the laser beam.

18. The modularized acoustic probe of claim 15, wherein the acoustic transducer is further configured to convert the reflected acoustic signal to a second electrical signal.

19. The modularized acoustic probe of claim 15, wherein:
   the first row of the two-row transducer array comprises a first number of acoustic transducers and the second row of the two-row transducer array comprises a second number of optical sensors;
   each acoustic transducer is configured to generate a respective acoustic signal and to transmit the respective acoustic signal toward the tissue or bone;
   each optical sensor is configured to detect reflected acoustic signals, which result from the respective acoustic signals reflecting from the tissue or bone, and to convert the reflected acoustic signals to respective electrical signals;
   each acoustic transducer and each optical sensor has a respective discrete substrate; and
   the first number and the second number are not same.

20. The modularized acoustic probe of claim 15, wherein the modularized acoustic probe includes a transducer combination in a shape of a disk;
   the transducer combination includes the acoustic transducer and the optical sensor;
   the acoustic transducer forms a first portion of the disk; and
   the optical sensor forms a second portion of the disk.

21. The modularized acoustic probe of claim 15, wherein the acoustic parameter includes at least one of the following:
   a center frequency;
   a resonant frequency;
   a dynamic range;
   a quality factor.

22. The modularized acoustic probe of claim 15, wherein the acoustic transducer and the optical sensor are configured to have at least a threshold difference in the acoustic parameter.

23. The modularized acoustic probe of claim 15, wherein:
   the acoustic parameter is a center frequency,
   the acoustic transducer has a first center frequency of X, and
   the optical sensor has a second center frequency of X*Y.

24. The modularized acoustic probe of claim 23, where X is a number selected from 3 MHZ, 3.5 MHz, 6 MHz, or 7.5 MHz, and Y is a number selected from 2, 12/7, 15/7, 2.5, or 3.

25. A method of making a modularized acoustic probe, the method comprising:
   fabricating a plurality of transducer sub-components having a plurality of respective discrete substrates;
   combining a first subset of the plurality of transducer sub-components to form an acoustic transducer disposed on a first substrate and configured to generate an acoustic signal and is further configured to transmit the acoustic signal toward tissue or bone;
   combining a second subset of the plurality of transducer sub-components to form an optical sensor disposed on a second substrate and configured to detect a reflected acoustic signal, which results from the acoustic signal reflecting from the tissue or bone, and is further configured to convert the reflected acoustic signal to an electrical signal, wherein the first substrate of the acoustic transducer and the second substrate of the optical sensor are discrete substrates and the acoustic transducer and the optical sensor have at least one different acoustic parameter;

combining the acoustic transducer and the optical sensor in a probe scanhead to form the modularized acoustic probe;

providing a thermal module disposed on the second substrate including at least one thermal circuit and configured to regulate a temperature inside the probe scanhead;

providing a first lens module associated with the acoustic transducer and configured to provide mechanical focusing of acoustic signals transmitted by the acoustic transducer; and providing a second lens module associated with the optical sensor having a different acoustic design than the first lens module and configured to provide mechanical focusing of acoustic signals received by the optical sensor.

26. The method of claim 25, wherein the acoustic parameter includes at least one of the following:
a center frequency;
a resonant frequency;
a dynamic range;
a quality factor.

27. The method of claim 25, wherein:
the acoustic parameter is a center frequency,
the acoustic transducer has a first center frequency of X, and
the optical sensor has a second center frequency of X*Y.

28. The method of claim 27, where X is a number selected from 3 MHz, 3.5 MHZ, 6 MHz, or 7.5 MHz, and Y is a number selected from 2, 12/7, 15/7, 2.5, or 3.

29. A method of making a modularized acoustic probe, the method comprising:
fabricating a plurality of transducer sub-components having a plurality of respective discrete substrates;
combining a first subset of the plurality of transducer sub-components to form an acoustic transducer disposed on a first substrate in a first row of a two-row transducer array, the acoustic transducer configured to generate an acoustic signal and further configured to transmit the acoustic signal toward tissue or bone;
combining a second subset of the plurality of transducer sub-components to form an optical sensor disposed on a second substrate in a second row of the two-row transducer array, the optical sensor configured to detect a reflected acoustic signal, which results from the acoustic signal reflecting from the tissue or bone, and further configured to convert the reflected acoustic signal to an electrical signal, wherein the first substrate of the acoustic transducer and the second substrate of the optical sensor are discrete substrates and the acoustic transducer and the optical sensor have at least one different acoustic parameter;
combining the first transducer and the second transducer in a probe scanhead to form the modularized acoustic probe; and
providing a thermal module disposed on the second substrate including at least one thermal circuit and configured to regulate a temperature inside the probe scanhead;

providing a first lens module associated with the acoustic transducer and configured to provide mechanical focusing of acoustic signals transmitted by the acoustic transducer; and providing a second lens module associated with the optical sensor having a different acoustic design than the first lens module and configured to provide mechanical focusing of acoustic signals received by the optical sensor.

30. The method of claim 29, wherein the acoustic parameter includes at least one of the following:
a center frequency;
a resonant frequency;
a dynamic range;
a quality factor.

31. The method of claim 29, wherein:
the acoustic parameter is a center frequency,
the acoustic transducer has a first center frequency of X, and
the optical sensor has a second center frequency of X*Y.

32. The method of claim 31, where X is a number selected from 3 MHz, 3.5 MHz, 6 MHz, or 7.5 MHz, and Y is a number selected from 2, 12/7, 15/7, 2.5, or 3.

33. A modularized acoustic probe comprising:
an acoustic transducer configured to generate an acoustic signal and to transmit the acoustic signal toward tissue or bone;
an optical sensor disposed on a second substrate and configured to detect a reflected acoustic signal, which results from the acoustic signal reflecting from the tissue or bone, and to convert the reflected acoustic signal to an electrical signal, wherein the first substrate of the acoustic transducer and the second substrate of the optical sensor are discrete substrates and the acoustic transducer and the optical sensor have at least one different acoustic parameter differing by a threshold difference; and
a thermal module disposed on the second substrate including at least one thermal circuit and configured to regulate a temperature of the optical sensor;
a first lens module associated with the acoustic transducer and configured to provide mechanical focusing of acoustic signals transmitted by the acoustic transducer; and
a second lens module associated with the optical sensor having a different acoustic design than the first lens module and configured to provide mechanical focusing of acoustic signals received by the optical sensor.

34. The modularized acoustic probe of claim 33, wherein the acoustic parameter includes at least one of the following:
a center frequency;
a resonant frequency;
a dynamic range;
a quality factor.

35. The modularized acoustic probe of claim 33, wherein:
the acoustic parameter is a center frequency,
the acoustic transducer has a first center frequency of X, and
the optical sensor has a second center frequency of X*Y.

36. The modularized acoustic probe of claim 35, where X is a number selected from 3 MHZ, 3.5 MHz, 6 MHz, or 7.5 MHZ, and Y is a number selected from 2, 12/7, 15/7, 2.5, or 3.

* * * * *